US009044185B2

(12) United States Patent
Bayer

(10) Patent No.: US 9,044,185 B2
(45) Date of Patent: Jun. 2, 2015

(54) METHOD AND DEVICE FOR EXAMINING OR IMAGING AN INTERIOR SURFACE OF A CAVITY

(75) Inventor: Lex Bayer, Palo Alto, CA (US)

(73) Assignee: Avantis Medical Systems, Inc., Sunnyvale, CA (US)

( * ) Notice: Subject to any disclaimer, the term of this patent is extended or adjusted under 35 U.S.C. 154(b) by 0 days.

(21) Appl. No.: 13/584,647

(22) Filed: Aug. 13, 2012

(65) Prior Publication Data
US 2012/0300999 A1  Nov. 29, 2012

Related U.S. Application Data

(63) Continuation of application No. 13/275,206, filed on Oct. 17, 2011, now abandoned, which is a continuation of application No. 12/101,050, filed on Apr. 10, 2008, now Pat. No. 8,064,666.

(60) Provisional application No. 60/911,054, filed on Apr. 10, 2007.

(51) Int. Cl.
G06K 9/00  (2006.01)
G06K 9/36  (2006.01)
A61B 1/31  (2006.01)
G06T 7/00  (2006.01)
A61B 1/00  (2006.01)
A61B 1/04  (2006.01)

(52) U.S. Cl.
CPC . *A61B 1/31* (2013.01); *G06T 7/004* (2013.01); G06T 2207/20212 (2013.01); G06T 2207/10068 (2013.01); A61B 1/042 (2013.01); *A61B 1/0005* (2013.01)

(58) Field of Classification Search
CPC .......... G06T 2207/20212; G06T 2207/30172; G06T 2210/04; A61B 19/5244; A61B 1/05
USPC .................................................. 382/128, 284
See application file for complete search history.

(56) References Cited

U.S. PATENT DOCUMENTS

| 3,437,747 A | 4/1969 | Sheldon |
| 3,610,231 A | 10/1971 | Takahashi et al. |
| 3,643,653 A | 2/1972 | Takahashi et al. |
| 3,739,770 A | 6/1973 | Mori |
| 3,889,662 A | 6/1975 | Mitsui |
| 3,897,775 A | 8/1975 | Furihata |

(Continued)

FOREIGN PATENT DOCUMENTS

| CN | 1628603 A | 6/2005 |
| DE | 196 26 433 A1 | 1/1998 |

(Continued)

OTHER PUBLICATIONS

Advisory Action mailed on Nov. 2, 2010, for U.S. Appl. No. 11/609,838, filed Dec. 12, 2006, 3 pages.

(Continued)

*Primary Examiner* — Utpal Shah
(74) *Attorney, Agent, or Firm* — Morrison & Foerster LLP

(57) ABSTRACT

A method for examining an interior surface of a cavity includes the steps of capturing partial images of an interior surface of a cavity; joining the captured partial images to form a complete image of said interior surface of the cavity; and providing an warning if the joined partial images does not form a complete image of said interior surface of the cavity.

20 Claims, 6 Drawing Sheets

(56) References Cited

U.S. PATENT DOCUMENTS

| | | |
|---|---|---|
| 3,918,438 A | 11/1975 | Hayamizu et al. |
| 4,066,071 A | 1/1978 | Nagel |
| 4,261,344 A | 4/1981 | Moore et al. |
| 4,351,587 A | 9/1982 | Matsuo et al. |
| 4,398,811 A | 8/1983 | Nishioka et al. |
| 4,494,549 A | 1/1985 | Namba et al. |
| 4,573,450 A | 3/1986 | Arakawa |
| 4,586,491 A | 5/1986 | Carpenter |
| 4,602,281 A | 7/1986 | Nagasaki et al. |
| 4,625,236 A | 11/1986 | Fujimori et al. |
| 4,646,722 A | 3/1987 | Silverstein et al. |
| 4,699,463 A | 10/1987 | D'Amelio et al. |
| 4,721,097 A | 1/1988 | D'Amelio |
| 4,727,859 A | 3/1988 | Lia |
| 4,741,326 A | 5/1988 | Sidall et al. |
| 4,742,817 A | 5/1988 | Kawashima et al. |
| 4,790,295 A | 12/1988 | Tashiro |
| 4,800,870 A | 1/1989 | Reid, Jr. |
| 4,825,850 A | 5/1989 | Opie et al. |
| 4,836,211 A | 6/1989 | Sekino et al. |
| 4,846,154 A | 7/1989 | MacAnally et al. |
| 4,852,551 A | 8/1989 | Opie et al. |
| 4,853,773 A | 8/1989 | Hibino et al. |
| 4,862,873 A | 9/1989 | Yajima et al. |
| 4,867,138 A | 9/1989 | Kubota et al. |
| 4,869,238 A | 9/1989 | Opie et al. |
| 4,870,488 A | 9/1989 | Ikuno et al. |
| 4,873,572 A | 10/1989 | Miyazaki et al. |
| 4,873,965 A | 10/1989 | Danieli |
| 4,884,133 A | 11/1989 | Kanno et al. |
| 4,899,732 A | 2/1990 | Cohen |
| 4,905,667 A | 3/1990 | Foerster et al. |
| 4,907,395 A | 3/1990 | Opie et al. |
| 4,911,148 A | 3/1990 | Sosnowski et al. |
| 4,911,564 A | 3/1990 | Baker |
| 4,926,258 A | 5/1990 | Sasaki |
| 4,947,827 A | 8/1990 | Opie et al. |
| 4,947,828 A | 8/1990 | Carpenter et al. |
| 4,979,496 A | 12/1990 | Komi |
| 4,991,565 A | 2/1991 | Takahashi et al. |
| 5,019,040 A | 5/1991 | Itaoka et al. |
| 5,025,778 A | 6/1991 | Silverstein et al. |
| 5,026,377 A | 6/1991 | Burton et al. |
| 5,050,585 A | 9/1991 | Takahashi |
| RE34,110 E | 10/1992 | Opie et al. |
| 5,159,446 A | 10/1992 | Hibino et al. |
| 5,166,787 A | 11/1992 | Irion |
| 5,178,130 A | 1/1993 | Kaiya et al. |
| 5,187,572 A | 2/1993 | Nakamura et al. |
| 5,193,525 A | 3/1993 | Silverstein et al. |
| 5,196,928 A | 3/1993 | Karasawa et al. |
| 5,253,638 A | 10/1993 | Tamburrino et al. |
| 5,260,780 A | 11/1993 | Staudt, III |
| 5,271,381 A | 12/1993 | Ailinger et al. |
| 5,305,121 A | 4/1994 | Moll |
| 5,318,031 A | 6/1994 | Mountford et al. |
| 5,329,887 A | 7/1994 | Ailinger et al. |
| 5,337,734 A | 8/1994 | Saab |
| 5,381,784 A | 1/1995 | Adair |
| 5,398,685 A * | 3/1995 | Wilk et al. ............... 600/437 |
| 5,406,938 A | 4/1995 | Mersch et al. |
| 5,434,669 A | 7/1995 | Tabata et al. |
| 5,443,781 A | 8/1995 | Saab |
| 5,447,148 A | 9/1995 | Oneda et al. |
| 5,483,951 A | 1/1996 | Frassica et al. |
| 5,494,483 A | 2/1996 | Adair |
| 5,518,501 A | 5/1996 | Oneda et al. |
| 5,520,607 A | 5/1996 | Frassica et al. |
| 5,530,238 A | 6/1996 | Meulenbrugge et al. |
| 5,533,496 A | 7/1996 | De Faria-Correa et al. |
| 5,536,236 A | 7/1996 | Yabe et al. |
| 5,556,367 A | 9/1996 | Yabe et al. |
| 5,613,936 A | 3/1997 | Czarnek et al. |
| 5,614,943 A | 3/1997 | Nakamura et al. |
| 5,626,553 A | 5/1997 | Frassica et al. |
| 5,634,466 A | 6/1997 | Gruner |
| 5,653,677 A | 8/1997 | Okada et al. |
| 5,667,476 A | 9/1997 | Frassica et al. |
| 5,679,216 A | 10/1997 | Takayama et al. |
| 5,681,260 A | 10/1997 | Ueda et al. |
| 5,682,199 A | 10/1997 | Lankford |
| 5,685,822 A | 11/1997 | Harhen |
| 5,692,729 A | 12/1997 | Harhen |
| 5,696,850 A | 12/1997 | Parulski et al. |
| 5,702,348 A | 12/1997 | Harhen |
| 5,706,128 A | 1/1998 | Greenberg |
| 5,711,299 A * | 1/1998 | Manwaring et al. .......... 600/417 |
| 5,722,933 A | 3/1998 | Yabe et al. |
| 5,752,912 A | 5/1998 | Takahashi et al. |
| 5,762,603 A | 6/1998 | Thompson |
| 5,817,061 A | 10/1998 | Goodwin et al. |
| 5,827,177 A | 10/1998 | Oneda et al. |
| 5,833,603 A | 11/1998 | Kovacs et al. |
| 5,843,103 A | 12/1998 | Wulfman |
| 5,843,460 A | 12/1998 | Labigne et al. |
| 5,854,859 A | 12/1998 | Sobol |
| 5,860,914 A | 1/1999 | Chiba et al. |
| 5,876,329 A | 3/1999 | Harhen |
| 5,916,147 A | 6/1999 | Boury |
| 5,924,977 A | 7/1999 | Yabe et al. |
| 5,938,587 A | 8/1999 | Taylor et al. |
| 5,982,932 A | 11/1999 | Prokoski |
| 5,989,182 A | 11/1999 | Hori et al. |
| 5,989,224 A | 11/1999 | Exline et al. |
| 6,017,358 A | 1/2000 | Yoon |
| 6,026,323 A | 2/2000 | Skladnev et al. |
| 6,066,090 A | 5/2000 | Yoon |
| 6,099,464 A | 8/2000 | Shimizu et al. |
| 6,099,466 A | 8/2000 | Sano et al. |
| 6,099,485 A | 8/2000 | Patterson |
| 6,106,463 A | 8/2000 | Wilk |
| 6,174,280 B1 | 1/2001 | Oneda et al. |
| 6,190,330 B1 | 2/2001 | Harhen |
| 6,214,028 B1 | 4/2001 | Yoon et al. |
| 6,261,226 B1 | 7/2001 | McKenna et al. |
| 6,261,307 B1 | 7/2001 | Yoon et al. |
| 6,277,064 B1 | 8/2001 | Yoon |
| 6,296,608 B1 | 10/2001 | Daniels et al. |
| 6,301,047 B1 | 10/2001 | Hoshino et al. |
| 6,350,231 B1 | 2/2002 | Ailinger et al. |
| 6,369,855 B1 | 4/2002 | Chauvel et al. |
| 6,375,653 B1 | 4/2002 | Desai |
| 6,387,043 B1 | 5/2002 | Yoon |
| 6,433,492 B1 | 8/2002 | Buonavita |
| 6,454,702 B1 | 9/2002 | Smith |
| 6,456,684 B1 | 9/2002 | Mun et al. |
| 6,461,294 B1 | 10/2002 | Oneda et al. |
| 6,464,633 B1 | 10/2002 | Hosoda et al. |
| 6,482,149 B1 | 11/2002 | Torii |
| 6,503,195 B1 | 1/2003 | Keller et al. |
| 6,527,704 B1 | 3/2003 | Chang et al. |
| 6,547,724 B1 | 4/2003 | Soble et al. |
| 6,554,767 B2 | 4/2003 | Tanaka |
| 6,564,088 B1 | 5/2003 | Soller et al. |
| 6,640,017 B1 | 10/2003 | Tsai et al. |
| 6,648,816 B2 | 11/2003 | Irion et al. |
| 6,683,716 B1 | 1/2004 | Costales |
| 6,687,010 B1 | 2/2004 | Horii et al. |
| 6,697,536 B1 | 2/2004 | Yamada |
| 6,699,180 B2 | 3/2004 | Kobayashi |
| 6,736,773 B2 | 5/2004 | Wendlandt et al. |
| 6,748,975 B2 | 6/2004 | Hartshorne et al. |
| 6,796,939 B1 | 9/2004 | Hirata et al. |
| 6,833,871 B1 | 12/2004 | Merrill et al. |
| 6,845,190 B1 | 1/2005 | Smithwick et al. |
| 6,891,977 B2 | 5/2005 | Gallagher |
| 6,916,286 B2 | 7/2005 | Kazakevich |
| 6,928,314 B1 * | 8/2005 | Johnson et al. ............... 600/407 |
| 6,929,636 B1 | 8/2005 | von Alten |
| 6,947,784 B2 * | 9/2005 | Zalis ............................. 600/425 |
| 6,951,536 B2 | 10/2005 | Yokoi et al. |
| 6,965,702 B2 | 11/2005 | Gallagher |
| 6,966,906 B2 | 11/2005 | Brown |
| 6,974,240 B2 | 12/2005 | Takahashi |

(56) References Cited

U.S. PATENT DOCUMENTS

| | | |
|---|---|---|
| 6,974,411 B2 | 12/2005 | Belson |
| 6,992,694 B2 | 1/2006 | Abe |
| 6,997,871 B2 | 2/2006 | Sonnenschein et al. |
| 7,004,900 B2 | 2/2006 | Wendlandt et al. |
| 7,029,435 B2 | 4/2006 | Nakao |
| 7,041,050 B1 | 5/2006 | Ronald |
| 7,095,548 B1 | 8/2006 | Cho et al. |
| 7,103,228 B2 | 9/2006 | Kraft et al. |
| 7,116,352 B2 | 10/2006 | Yaron |
| 7,173,656 B1 | 2/2007 | Dunton et al. |
| 7,228,004 B2 | 6/2007 | Gallagher et al. |
| 7,258,663 B2 | 8/2007 | Doguchi et al. |
| 7,280,141 B1 | 10/2007 | Frank et al. |
| 7,317,458 B2 | 1/2008 | Wada |
| 7,322,934 B2 | 1/2008 | Miyake et al. |
| 7,341,555 B2 | 3/2008 | Ootawara et al. |
| 7,362,911 B1 | 4/2008 | Frank |
| 7,389,892 B2 | 6/2008 | Park |
| 7,405,877 B1 | 7/2008 | Schechterman |
| 7,435,218 B2 | 10/2008 | Krattiger et al. |
| 7,436,562 B2 | 10/2008 | Nagasawa et al. |
| 7,507,200 B2 | 3/2009 | Okada |
| 7,551,196 B2 | 6/2009 | Ono et al. |
| 7,556,599 B2 | 7/2009 | Rovegno |
| 7,561,190 B2 | 7/2009 | Deng et al. |
| 7,621,869 B2 | 11/2009 | Ratnakar |
| 7,646,520 B2 | 1/2010 | Funaki et al. |
| 7,678,043 B2 | 3/2010 | Gilad |
| 7,683,926 B2 | 3/2010 | Schechterman et al. |
| 7,749,156 B2 | 7/2010 | Ouchi |
| 7,825,964 B2 | 11/2010 | Hoshino et al. |
| 7,864,215 B2 | 1/2011 | Carlsson et al. |
| 7,910,295 B2 | 3/2011 | Hoon et al. |
| 7,927,272 B2 | 4/2011 | Bayer et al. |
| 8,009,167 B2 * | 8/2011 | Dekel et al. .................. 345/420 |
| 8,064,666 B2 | 11/2011 | Bayer |
| 8,070,743 B2 | 12/2011 | Kagan et al. |
| 8,182,422 B2 | 5/2012 | Bayer et al. |
| 8,197,399 B2 | 6/2012 | Bayer et al. |
| 8,235,887 B2 | 8/2012 | Bayer et al. |
| 8,287,446 B2 | 10/2012 | Bayer |
| 8,289,381 B2 | 10/2012 | Bayer et al. |
| 8,310,530 B2 | 11/2012 | Bayer et al. |
| 8,587,645 B2 | 11/2013 | Bayer et al. |
| 8,797,392 B2 | 8/2014 | Bayer et al. |
| 8,872,906 B2 | 10/2014 | Bayer et al. |
| 2001/0007468 A1 | 7/2001 | Sugimoto et al. |
| 2001/0031912 A1 | 10/2001 | Adler |
| 2001/0037052 A1 | 11/2001 | Higuchi et al. |
| 2001/0051766 A1 | 12/2001 | Gazdinski |
| 2001/0056238 A1 | 12/2001 | Tsujita |
| 2002/0026188 A1 | 2/2002 | Balbierz et al. |
| 2002/0039400 A1 | 4/2002 | Kaufman et al. |
| 2002/0089584 A1 | 7/2002 | Abe |
| 2002/0095168 A1 | 7/2002 | Griego et al. |
| 2002/0099267 A1 | 7/2002 | Wendlandt et al. |
| 2002/0101546 A1 | 8/2002 | Sharp et al. |
| 2002/0103420 A1 | 8/2002 | Coleman et al. |
| 2002/0110282 A1 | 8/2002 | Kraft et al. |
| 2002/0115908 A1 | 8/2002 | Farkas et al. |
| 2002/0156347 A1 | 10/2002 | Kim et al. |
| 2002/0165444 A1 | 11/2002 | Whitman |
| 2002/0193662 A1 | 12/2002 | Belson |
| 2003/0001951 A1 | 1/2003 | Tsujita et al. |
| 2003/0004399 A1 | 1/2003 | Belson |
| 2003/0011768 A1 | 1/2003 | Jung et al. |
| 2003/0032863 A1 | 2/2003 | Kazakevich et al. |
| 2003/0040668 A1 | 2/2003 | Kaneko et al. |
| 2003/0045778 A1 | 3/2003 | Ohline et al. |
| 2003/0065250 A1 | 4/2003 | Chiel et al. |
| 2003/0088152 A1 | 5/2003 | Takada |
| 2003/0093031 A1 | 5/2003 | Long et al. |
| 2003/0093088 A1 | 5/2003 | Long et al. |
| 2003/0103199 A1 | 6/2003 | Jung et al. |
| 2003/0105386 A1 | 6/2003 | Voloshin et al. |
| 2003/0120130 A1 | 6/2003 | Glukhovsky |
| 2003/0125630 A1 | 7/2003 | Furnish |
| 2003/0128892 A1 | 7/2003 | Avinash |
| 2003/0130711 A1 | 7/2003 | Pearson et al. |
| 2003/0153866 A1 | 8/2003 | Long et al. |
| 2003/0161545 A1 | 8/2003 | Gallagher |
| 2003/0167007 A1 * | 9/2003 | Belson ......................... 600/473 |
| 2003/0171650 A1 | 9/2003 | Tartaglia et al. |
| 2003/0176767 A1 | 9/2003 | Long et al. |
| 2003/0179302 A1 | 9/2003 | Harada et al. |
| 2003/0187326 A1 | 10/2003 | Chang |
| 2003/0195545 A1 | 10/2003 | Hermann et al. |
| 2003/0197781 A1 | 10/2003 | Sugimoto et al. |
| 2003/0197793 A1 | 10/2003 | Mitsunaga et al. |
| 2003/0215788 A1 | 11/2003 | Long |
| 2003/0225433 A1 | 12/2003 | Nakao |
| 2003/0233115 A1 | 12/2003 | Eversull et al. |
| 2004/0015049 A1 | 1/2004 | Zaar |
| 2004/0023397 A1 | 2/2004 | Vig et al. |
| 2004/0034278 A1 | 2/2004 | Adams |
| 2004/0049096 A1 | 3/2004 | Adams |
| 2004/0059191 A1 | 3/2004 | Krupa et al. |
| 2004/0080613 A1 | 4/2004 | Moriyama |
| 2004/0085443 A1 | 5/2004 | Kallioniemi et al. |
| 2004/0097790 A1 | 5/2004 | Farkas et al. |
| 2004/0109164 A1 | 6/2004 | Horii et al. |
| 2004/0109319 A1 | 6/2004 | Takahashi |
| 2004/0111019 A1 | 6/2004 | Long |
| 2004/0122291 A1 | 6/2004 | Takahashi |
| 2004/0141054 A1 | 7/2004 | Mochida et al. |
| 2004/0158124 A1 | 8/2004 | Okada |
| 2004/0207618 A1 | 10/2004 | Williams et al. |
| 2004/0228544 A1 | 11/2004 | Endo et al. |
| 2004/0242987 A1 | 12/2004 | Liew et al. |
| 2005/0010084 A1 | 1/2005 | Tsai |
| 2005/0014996 A1 | 1/2005 | Konomura et al. |
| 2005/0020918 A1 | 1/2005 | Wilk et al. |
| 2005/0020926 A1 | 1/2005 | Wiklof et al. |
| 2005/0038317 A1 | 2/2005 | Ratnakar |
| 2005/0038319 A1 | 2/2005 | Goldwasser et al. |
| 2005/0068431 A1 | 3/2005 | Mori |
| 2005/0085693 A1 | 4/2005 | Belson et al. |
| 2005/0085790 A1 | 4/2005 | Guest et al. |
| 2005/0096502 A1 | 5/2005 | Khalili |
| 2005/0154278 A1 | 7/2005 | Cabiri et al. |
| 2005/0165272 A1 | 7/2005 | Okada et al. |
| 2005/0165279 A1 | 7/2005 | Adler et al. |
| 2005/0177024 A1 | 8/2005 | Mackin |
| 2005/0203420 A1 | 9/2005 | Kleen et al. |
| 2005/0215911 A1 | 9/2005 | Alfano et al. |
| 2005/0222500 A1 | 10/2005 | Itoi |
| 2005/0228224 A1 | 10/2005 | Okada et al. |
| 2005/0267361 A1 | 12/2005 | Younker et al. |
| 2005/0272975 A1 | 12/2005 | McWeeney et al. |
| 2005/0272977 A1 | 12/2005 | Saadat et al. |
| 2006/0044267 A1 | 3/2006 | Xie et al. |
| 2006/0052709 A1 | 3/2006 | DeBaryshe et al. |
| 2006/0058584 A1 | 3/2006 | Hirata |
| 2006/0106286 A1 | 5/2006 | Wendlandt et al. |
| 2006/0114986 A1 | 6/2006 | Knapp et al. |
| 2006/0149127 A1 | 7/2006 | Seddiqui et al. |
| 2006/0149129 A1 | 7/2006 | Watts et al. |
| 2006/0183975 A1 | 8/2006 | Saadat et al. |
| 2006/0184037 A1 | 8/2006 | Ince et al. |
| 2006/0217594 A1 | 9/2006 | Ferguson |
| 2006/0238614 A1 | 10/2006 | Konno |
| 2006/0250503 A1 | 11/2006 | Crutchfield et al. |
| 2006/0252994 A1 | 11/2006 | Ratnakar |
| 2006/0279632 A1 | 12/2006 | Anderson |
| 2006/0280360 A1 | 12/2006 | Holub |
| 2006/0285766 A1 | 12/2006 | Ali |
| 2006/0293562 A1 | 12/2006 | Uchimura et al. |
| 2007/0015967 A1 * | 1/2007 | Boulais et al. ................ 600/146 |
| 2007/0015989 A1 | 1/2007 | Desai et al. |
| 2007/0066868 A1 | 3/2007 | Shikii |
| 2007/0083081 A1 | 4/2007 | Schlagenhauf et al. |
| 2007/0097206 A1 | 5/2007 | Houvener et al. |
| 2007/0103460 A1 * | 5/2007 | Zhang et al. .................. 345/419 |
| 2007/0118017 A1 | 5/2007 | Honda |

(56) References Cited

U.S. PATENT DOCUMENTS

| | | |
|---|---|---|
| 2007/0142711 A1 | 6/2007 | Bayer et al. |
| 2007/0173686 A1 | 7/2007 | Lin et al. |
| 2007/0177008 A1 | 8/2007 | Bayer et al. |
| 2007/0177009 A1 | 8/2007 | Bayer et al. |
| 2007/0183685 A1* | 8/2007 | Wada et al. ............ 382/285 |
| 2007/0185384 A1 | 8/2007 | Bayer et al. |
| 2007/0225552 A1 | 9/2007 | Segawa et al. |
| 2007/0225554 A1 | 9/2007 | Maseda et al. |
| 2007/0225734 A1 | 9/2007 | Bell et al. |
| 2007/0238927 A1 | 10/2007 | Ueno et al. |
| 2007/0244354 A1 | 10/2007 | Bayer |
| 2007/0270642 A1 | 11/2007 | Bayer et al. |
| 2007/0279486 A1 | 12/2007 | Bayer et al. |
| 2007/0280669 A1 | 12/2007 | Karim |
| 2007/0293720 A1 | 12/2007 | Bayer |
| 2008/0021269 A1 | 1/2008 | Tinkham et al. |
| 2008/0021274 A1 | 1/2008 | Bayer et al. |
| 2008/0033450 A1 | 2/2008 | Bayer et al. |
| 2008/0039693 A1 | 2/2008 | Karasawa |
| 2008/0064931 A1 | 3/2008 | Schena et al. |
| 2008/0065110 A1 | 3/2008 | Duval et al. |
| 2008/0071291 A1 | 3/2008 | Duval et al. |
| 2008/0079827 A1 | 4/2008 | Hoshino et al. |
| 2008/0084478 A1 | 4/2008 | Gilad et al. |
| 2008/0097292 A1 | 4/2008 | Cabiri et al. |
| 2008/0114288 A1 | 5/2008 | Whayne et al. |
| 2008/0130108 A1 | 6/2008 | Bayer et al. |
| 2008/0154288 A1 | 6/2008 | Belson |
| 2008/0199829 A1* | 8/2008 | Paley et al. ............ 433/215 |
| 2008/0200763 A1 | 8/2008 | Ueno |
| 2008/0275298 A1 | 11/2008 | Ratnakar |
| 2009/0015842 A1 | 1/2009 | Leitgeb et al. |
| 2009/0023998 A1 | 1/2009 | Ratnakar |
| 2009/0028407 A1 | 1/2009 | Seibel et al. |
| 2009/0036739 A1 | 2/2009 | Hadani |
| 2009/0049627 A1 | 2/2009 | Kritzler |
| 2009/0082629 A1 | 3/2009 | Dotan et al. |
| 2009/0105538 A1 | 4/2009 | Van Dam et al. |
| 2009/0137867 A1 | 5/2009 | Goto |
| 2009/0208071 A1 | 8/2009 | Nishimura et al. |
| 2009/0213211 A1 | 8/2009 | Bayer et al. |
| 2009/0231419 A1 | 9/2009 | Bayer |
| 2010/0217076 A1 | 8/2010 | Ratnakar |
| 2011/0160535 A1 | 6/2011 | Bayer et al. |
| 2011/0213206 A1 | 9/2011 | Boutillette et al. |
| 2012/0033062 A1 | 2/2012 | Bayer |
| 2012/0053407 A1 | 3/2012 | Levy |
| 2012/0065468 A1 | 3/2012 | Levy et al. |
| 2012/0209071 A1 | 8/2012 | Bayer et al. |
| 2012/0224026 A1 | 9/2012 | Bayer et al. |
| 2012/0229615 A1 | 9/2012 | Kirma et al. |
| 2012/0232340 A1 | 9/2012 | Levy et al. |
| 2012/0232343 A1 | 9/2012 | Levy et al. |
| 2012/0232345 A1 | 9/2012 | Levy et al. |
| 2013/0012778 A1 | 1/2013 | Bayer et al. |
| 2013/0116506 A1 | 5/2013 | Bayer et al. |
| 2014/0018624 A1 | 1/2014 | Bayer et al. |
| 2014/0046136 A1 | 2/2014 | Bayer et al. |
| 2014/0336459 A1 | 11/2014 | Bayer et al. |

FOREIGN PATENT DOCUMENTS

| | | | |
|---|---|---|---|
| DE | 20 2006 017 173 U1 | | 3/2007 |
| EP | 0 586 162 A1 | | 3/1994 |
| EP | 1 570 778 A1 | | 9/2005 |
| EP | 1 769 720 A1 | | 4/2007 |
| FR | 711 949 | | 9/1931 |
| JP | 49-130235 A | | 12/1974 |
| JP | 56-9712 A | | 1/1981 |
| JP | 56-56486 A | | 5/1981 |
| JP | 57-170707 | | 10/1982 |
| JP | 60-83636 A | | 5/1985 |
| JP | 60-111217 A | | 6/1985 |
| JP | 62-094312 U1 | | 6/1987 |
| JP | 63-309912 A | | 12/1988 |
| JP | 1-267514 A | | 10/1989 |
| JP | 1-172847 U | | 12/1989 |
| JP | 2-295530 A | | 12/1990 |
| JP | 3-159629 A | | 7/1991 |
| JP | 4-500768 A | | 2/1992 |
| JP | 4-341232 A | | 11/1992 |
| JP | 5-285091 A | | 11/1993 |
| JP | 5-307144 A | | 11/1993 |
| JP | 5-341210 A | | 12/1993 |
| JP | 6-9228 B2 | | 2/1994 |
| JP | 60-76714 A | | 3/1994 |
| JP | 6-130308 A | | 5/1994 |
| JP | 6-169880 A | | 6/1994 |
| JP | 7-352 A | | 1/1995 |
| JP | 7-354 A | | 1/1995 |
| JP | 7-021001 U | | 4/1995 |
| JP | 7-136108 A | | 5/1995 |
| JP | 7-275197 A | | 10/1995 |
| JP | 8-024208 A2 | | 1/1996 |
| JP | 8-206061 A | | 8/1996 |
| JP | 9-56662 A | | 3/1997 |
| JP | 11-76150 A | | 3/1999 |
| JP | 11-253401 A | | 9/1999 |
| JP | 11-332821 A | | 12/1999 |
| JP | 2003-135388 A | | 5/2003 |
| JP | 2003-220023 A | | 8/2003 |
| JP | 2004-202252 A | | 7/2004 |
| JP | 2004-525717 A | | 8/2004 |
| JP | 2004-537362 A | | 12/2004 |
| JP | 2007-143580 A | | 6/2007 |
| WO | WO-93/15648 A1 | | 8/1993 |
| WO | WO-99/17542 A1 | | 4/1999 |
| WO | WO-99/30506 A1 | | 6/1999 |
| WO | WO-02/085194 A1 | | 10/2002 |
| WO | WO-02/094105 A2 | | 11/2002 |
| WO | WO-02/094105 A3 | | 11/2002 |
| WO | WO-03/013349 A2 | | 2/2003 |
| WO | WO-2006/073676 A1 | | 7/2006 |
| WO | WO-2006/073725 A1 | | 7/2006 |
| WO | WO-2006/087981 A1 | | 8/2006 |
| WO | WO-2006/110275 A2 | | 10/2006 |
| WO | WO-2006/110275 A3 | | 10/2006 |
| WO | WO-2007/015241 A2 | | 2/2007 |
| WO | WO-2007/015241 A3 | | 2/2007 |
| WO | WO-2007/070644 A2 | | 6/2007 |
| WO | WO-2007/070644 A3 | | 6/2007 |
| WO | WO-2007/087421 A2 | | 8/2007 |
| WO | WO-2007/087421 A3 | | 8/2007 |
| WO | WO-2007/092533 A2 | | 8/2007 |
| WO | WO-2007/092533 A3 | | 8/2007 |
| WO | WO-2007/092636 A2 | | 8/2007 |
| WO | WO-2007/092636 A3 | | 8/2007 |
| WO | WO-2007/136859 A2 | | 11/2007 |
| WO | WO-2007/136859 A3 | | 11/2007 |
| WO | WO-2007/136879 A2 | | 11/2007 |
| WO | WO-2007/136879 A3 | | 11/2007 |
| WO | WO-2007/136879 B1 | | 11/2007 |
| WO | WO-2009/014895 A1 | | 1/2009 |
| WO | WO-2009/015396 A2 | | 1/2009 |
| WO | WO-2009/015396 A3 | | 1/2009 |
| WO | WO-2009/049322 A2 | | 4/2009 |
| WO | WO-2009/049322 A3 | | 4/2009 |
| WO | WO-2009/049324 A1 | | 4/2009 |
| WO | WO-2009/062179 A1 | | 5/2009 |

OTHER PUBLICATIONS

Advisory Action mailed on May 23, 2011, for U.S. Appl. No. 11/751,605, filed May 21, 2007, 3 pages.

Amendment in Response to Non-Final Office Action filed on Jun. 29, 2009, for U.S. Appl. No. 11/215,660, filed Aug. 29, 2005, 9 pages.

Amendment in Response to Final Office Action filed on Mar. 8, 2010, for U.S. Appl. No. 11/215,660, filed Aug. 29, 2005, 11 pages.

Amendment in Response to Non-Final Office Action filed on Jun. 25, 2010, for U.S. Appl. No. 11/609,838, filed Dec. 12, 2006, 14 pages.

Amendment in Response to Non-Final Office Action filed on Aug. 30, 2010, for U.S. Appl. No. 11/215,660, filed Aug. 29, 2005, 17 pages.

(56) References Cited

OTHER PUBLICATIONS

Amendment in Response to Final Office Action filed on Oct. 22, 2010, for U.S. Appl. No. 11/609,838, filed Dec. 12, 2006, 15 pages.
Amendment in Response to Non-Final Office Action filed on Oct. 22, 2010, for U.S. Appl. No. 11/834,540, filed Aug. 6, 2007, 13 pages.
Amendment in Response to Non-Final Office Action filed on Feb. 9, 2011, for U.S. Appl. No. 11/828,835, filed Jul. 26, 2007, 10 pages.
Amendment in Response to Non-Final Office Action filed on Feb. 25, 2011, for U.S. Appl. No. 11/751,605, filed May 21, 2007, 15 pages.
Amendment in Response to Final Office Action filed on Feb. 28, 2011, for U.S. Appl. No. 11/215,660, filed Aug. 29, 2005, 11 pages.
Amendment in Response to Non-Final Office Action filed on Apr. 12, 2011, for U.S. Appl. No. 11/626,189, filed Jan. 23, 2007, 18 pages.
Amendment in Response to Non-Final Office Action filed on May 17, 2011, for U.S. Appl. No. 11/609,838, filed Dec. 12, 2006, 18 pages.
Amendment in Response to Final Office Action filed on May 17, 2011, for U.S. Appl. No. 11/751,605, filed May 21, 2007, 10 pages.
Amendment in Response to Final Office Action filed on May 24, 2011, for U.S. Appl. No. 11/828,835, filed Jul. 26, 2007, 13 pages.
Amendment in Response to Non-Final Office Action filed on May 23, 2011, for U.S. Appl. No. 11/736,438, filed Apr. 17, 2007, 11 pages.
Amendment in Response to Non-Final Office Action filed on Jun. 6, 2011, for U.S. Appl. No. 12/101,050, filed Apr. 10, 2008, 17 pages.
Amendment in response to Final Office Action filed on Jun. 7, 2011, for U.S. Appl. No. 11/751,605, filed May 21, 2007, 11 pages.
Amendment in Response to Final Office Action filed on Dec. 7, 2011, for U.S. Appl. No. 11/736,438, filed Apr. 17, 2007, 10 pages.
Amendment in Response to Non-Final Office Action filed on Dec. 16, 2011, for U.S. Appl. No. 11/938,256, filed Nov. 10, 2007, 10 pages.
Amendment in Response to Non-Final Office Action filed on Jan. 9, 2012, for U.S. Appl. No. 11/751,596, filed May 21, 2007, 9 pages.
Amendment in Response to Non-Final Office Action filed on Feb. 15, 2012, for U.S. Appl. No. 11/626,189, filed Jan. 23, 2007, 13 pages.
Amendment in Response to Non-Final Office Action filed on Feb. 17, 2012, for U.S. Appl. No. 11/751,597, filed May 21, 2007, 18 pages.
Amendment in Response to Non-Final Office Action filed on Mar. 23, 2012, for U.S. Appl. No. 11/672,020, filed Feb. 6, 2007, 12 pages.
European Communication mailed on Jan. 22, 2009, for European Application No. 07777255.6, filed May 21, 2007, 2 pages.
European Office Action mailed on May 5, 2009, for European Patent Application No. 07763368.3, filed on Feb. 6, 2007, 3 pages.
European Office Action mailed on Feb. 5, 2010, for European Patent Application No. 06845440.4, filed on Dec. 13, 2006, 4 pages.
European Office Action mailed on Apr. 1, 2010, for European Patent Application No. 07717235.1, filed on Feb. 9, 2007, 2 pages.
European Office Action mailed on Nov. 8, 2010, for European Patent Application No. 05854262.2, filed on Dec. 8, 2005, 5 pages.
European Office Action mailed on Jun. 14, 2011, for European Patent Application No. 07795177.0, filed on May 21, 2007, 6 pages.
Final Office Action mailed on Oct. 8, 2009, for U.S. Appl. No. 11/215,660, filed Aug. 29, 2005, 12 pages.
Final Office Action mailed on Aug. 23, 2010, for U.S. Appl. No. 11/609,838, filed Dec. 12, 2006, 20 pages.
Final Office Action mailed on Nov. 1, 2010, for U.S. Appl. No. 11/215,660, filed Aug. 29, 2005, 12 pages.
Final Office Action mailed on Mar. 22, 2011, for U.S. Appl. No. 11/828,835, filed Jul. 26, 2007, 11 pages.
Final Office Action mailed on Apr. 29, 2011, for U.S. Appl. No. 11/751,605, filed May 21, 2007, 9 pages.
Final Office Action mailed on Aug. 3, 2011, for U.S. Appl. No. 11/736,438, filed Apr. 17, 2007, 11 pages.
Final Office Action mailed on Apr. 25, 2012, for U.S. Appl. No. 12/251,406, filed Oct. 14, 2008, 10 pages.
International Search Report mailed on May 18, 2006, for PCT Patent Application No. PCT/US2005/045499, filed on Dec. 8, 2005, 4 pages.
International Search Report mailed on May 19, 2006, for PCT Patent Application No. PCT/US2005/044624, filed on Dec. 8, 2005, 4 pages.
International Search Report mailed on Jun. 20, 2007, for PCT Patent Application No. PCT/US2006/047748, filed on Dec. 13, 2006, 3 pages.
International Search Report mailed on Sep. 28, 2007, for PCT Patent Application No. PCT/US2007/002096 filed on Jan. 23, 2007, 4 pages.
International Search Report mailed on Oct. 25, 2007, for PCT Patent Application No. PCT/US2007/003322, filed on Feb. 6, 2007, 5 pages.
International Search Report mailed on Oct. 26, 2007, for PCT Patent Application No. PCT/US2007/003631, filed on Feb. 9, 2007, 5 pages.
International Search Report mailed on Dec. 11, 2007, for PCT Patent Application No. PCT/US2007/012358, filed on May 21, 2007, 3 pages.
International Search Report mailed on Jan. 28, 2008, for PCT Patent Application No. PCT/US2007/012189, filed on May 21, 2007, 2 pages.
International Search Report mailed on Oct. 23, 2008, for PCT Patent Application No. PCT/US2008/069435, filed on Jul. 8, 2008, 4 pages.
International Search Report mailed on Feb. 25, 2009, for PCT Patent Application No. PCT/US2008/071390, filed on Jul. 28, 2008, 2 pages.
International Search Report mailed on Mar. 13, 2009, for PCT Patent Application No. PCT/US2008/083034, filed on Nov. 10, 2008, 2 pages.
International Search Report mailed on Mar. 13, 2009, for PCT Patent Application No. PCT/US2008/079891, filed on Nov. 10, 2008, 2 pages.
International Search Report mailed on Apr. 6, 2009, for PCT Patent Application No. PCT/US2008/079878, filed on Oct. 14, 2008, 3 pages.
Invitation to Pay Additional Fees mailed on Jul. 6, 2007, for PCT Patent Application No. PCT/US2007/002096, filed on Jan. 23, 2007, 4 pages.
Invitation to Pay Additional Fees mailed on Aug. 7, 2007, for PCT Patent Application No. PCT/US2007/003322, filed on Feb. 6, 2007, 5 pages.
Invitation to Pay Additional Fees mailed on Aug. 7, 2007, for PCT Patent Application No. PCT/US2007/003631, filed on Feb. 9, 2007, 5 pages.
Invitation to Pay Additional Fees mailed on Nov. 11, 2008, for PCT Patent Application No. PCT/US2008/071390, filed on Jul. 28, 2008, 5 pages.
Invitation to Pay Additional Fees mailed on Dec. 29, 2008, for PCT Patent Application No. PCT/US2008/079891, filed on Oct. 14, 2008, 7 pages.
Japanese Office Action mailed on Jul. 19, 2011, for Japanese Patent Application No. 2007-550378, filed on Dec. 8, 2005, with English Translation, 11 pages.
Japanese Office Action mailed Feb. 28, 2012, for Japanese Patent Application No. 2008-545817, filed on Dec. 13, 2006, with English Translation, 6 pages.
Japanese Office Action mailed on Feb. 28, 2012, for Japanese Patent Application No. 2008-551487, filed on Jan. 23, 2007, with English Translation, 9 pages.
Japanese Office Action mailed on Feb. 28, 2012, for Japanese Patent Application No. 2008-554410, filed on Feb. 9, 2007, with English Translation, 6 pages.
Japanese Office Action mailed on Mar. 6, 2012, for Japanese Patent Application No. 2008-553430, filed on Feb. 6, 2007, with English Translation, 6 pages.
Japanese Office Action mailed on Jan. 15, 2013, for Japanese Patent Application No. 2010-518438, filed on Jan. 25, 2010, with English Translation, 7 pages.
Non-Final Office Action mailed on Jan. 10, 2008, for U.S. Appl. No. 11/160,646, filed Jul. 1, 2005, 6 pages.
Non-Final Office Action mailed on Mar. 12, 2008, for U.S. Appl. No. 11/153,007, filed Jun. 14, 2005, 11 pages.
Non-Final Office Action mailed on Mar. 25, 2009, for U.S. Appl. No. 11/215,660, filed Aug. 29, 2005, 11 pages.
Non-Final Office Action mailed on Mar. 29, 2010, for U.S. Appl. No. 11/215,660, filed Aug. 29, 2005, 16 pages.
Non-Final Office Action mailed on Apr. 6, 2010, for U.S. Appl. No. 11/609,838, filed Dec. 12, 2006, 25 pages.

(56) References Cited

OTHER PUBLICATIONS

Non-Final Office Action mailed on Aug. 24, 2010, for U.S. Appl. No. 11/834,540, filed Aug. 6, 2007, 11 pages.
Non-Final Office Action mailed on Oct. 18, 2010, for U.S. Appl. No. 11/626,189, filed Jan. 23, 2007, 11 pages.
Non-Final Office Action mailed on Oct. 28, 2010, for U.S. Appl. No. 11/828,835, filed Jul. 26, 2007, 11 pages.
Non-Final Office Action mailed on Dec. 22, 2010, for U.S. Appl. No. 11/751,605, filed May 21, 2007, 10 pages.
Non-Final Office Action mailed on Feb. 17, 2011, for U.S. Appl. No. 11/609,838, filed Dec. 12, 2006, 24 pages.
Non-Final Office Action mailed on Mar. 2, 2011, for U.S. Appl. No. 11/736,438, filed Apr. 17, 2007, 10 pages.
Non-Final Office Action mailed on May 23, 2011, for U.S. Appl. No. 12/101,050, filed Apr. 10, 2008, 11 pages.
Non-Final Office Action mailed on Jun. 28, 2011, for U.S. Appl. No. 11/938,256, filed Nov. 10, 2007, 23 pages.
Non-Final Office Action mailed on Aug. 4, 2011, for U.S. Appl. No. 11/609,838, filed Dec. 12, 2006, 16 pages.
Non-Final Office Action mailed on Aug. 15, 2011, for U.S. Appl. No. 11/626,189, filed Jan. 23, 2007, 13 pages.
Non-Final Office Action mailed on Aug. 18, 2011, for U.S. Appl. No. 11/751,597, filed May 21, 2007, 25 pages.
Non-Final Office Action mailed on Sep. 9, 2011, for U.S. Appl. No. 11/751,596, filed May 21, 2007, 6 pages.
Non-Final Office Action mailed on Oct. 21, 2011, for PCT U.S. Appl. No. 12/251,406, filed Oct. 14, 2008, 8 pages.
Non-Final Office Action mailed on Oct. 26, 2011, for U.S. Appl. No. 11/673,470, filed Feb. 9, 2007, 40 pages.
Non-Final Office Action mailed on Nov. 23, 2011, for U.S. Appl. No. 11/672,020, filed Feb. 6, 2007, 12 pages.
Non-Final Office Action mailed on Feb. 13, 2012, for U.S. Appl. No. 13/275,206, filed Oct. 17, 2011, 13 pages.
Non-Final Office Action mailed on Feb. 14, 2012, for U.S Appl. No. 12/251,383, filed Oct. 14, 2008, 9 pages.
Non-Final Office Action mailed on Jun. 22, 2012, for U.S. Appl. No. 12/181,280, filed Jul. 28, 2008, 12 pages.
Notice of Allowance mailed on Dec. 13, 2010, for U.S. Appl. No. 11/834,540, filed Aug. 6, 2007, 4 pages.
Notice of Allowance mailed on Jul. 22, 2011, for U.S. Appl. No. 12/101,050, filed Apr. 10, 2008, 7 pages.
Notice of Allowance mailed on Feb. 8, 2012, for U.S. Appl. No. 11/609,838, filed Dec. 12, 2006, 8 pages.
Notice of Allowance mailed on Feb. 29, 2012, for U.S. Appl. No. 11/751,596, filed May 21, 2007, 10 pages.
Notice of Allowance mailed on Mar. 14, 2012, for U.S. Appl. No. 11/626,189, filed Jan. 23, 2007, 13 pages.
Notice of Allowance mailed on Jun. 7, 2012, for U.S. Appl. No. 11/751,597, filed May 21, 2007, 17 pages.
Notice of Allowance mailed on Jul. 19, 2013, for U.S. Appl. No. 13/606,465, filed Sep. 7, 2012, 14 pages.
Preliminary Amendment filed Jan. 26, 2009, for U.S. Appl. No. 11/672,020, filed Feb. 6, 2007, 11 pages.
Response to European Communication filed Feb. 6, 2009, for European Patent Application No. 07777255.6, filed on May 21, 2007, 5 pages.
Response to European Office Action filed on Nov. 11, 2009, for European Patent Application No. 07783368.3, filed on Feb. 6, 2007, 12 pages.
Response to European Office Action filed on Jul. 7, 2010, for European Patent Application No. 06845440.4, filed on Dec. 13, 2006, 13 pages.
Response to European Office Action filed on Aug. 18, 2010, for European Patent Application No. 07717235.1, filed on Feb. 9, 2007, 7 pages.
Response to European Office Action filed on Mar. 8, 2011, for European Patent Application No. 05854262.2, filed on Dec. 8, 2005, 11 pages.
Response to European Office Action filed on Dec. 13, 2011, for European Patent Application No. 07795177.0, filed on May 21, 2007, 9 pages.
Response to Restriction Requirement filed on Jan. 26, 2009, for U.S. Appl. No. 11/215,660, filed Aug. 29, 2005, 2 pages.
Response to Restriction Requirement filed on Jul. 23, 2010, for U.S. Appl. No. 11/751,605, filed May 21, 2007, 9 pages.
Response to Restriction Requirement filed on Aug. 4, 2010, for U.S. Appl. No. 11/834,540, filed Aug. 6, 2007, 5 pages.
Response to Restriction Requirement filed on Sep. 9, 2010, for U.S. Appl. No. 11/626,189, filed Jan. 23, 2007, 8 pages.
Response to Restriction Requirement filed on Oct. 21, 2010, for U.S. Appl. No. 11/828,835, filed Jul. 26, 2007, 7 pages.
Response to Restriction Requirement filed on Feb. 8, 2011, for U.S. Appl. No. 11/736,438, filed Apr. 17, 2007, 8 pages.
Response to Restriction Requirement filed on Apr. 27, 2011, for U.S. Appl. No. 12/101,050, filed Apr. 10, 2008, 13 pages.
Response to Restriction Requirement filed on Jun. 16, 2011, for U.S. Appl. No. 11/751,596, filed May 21, 2007, 8 pages.
Response to Restriction Requirement filed on Oct. 31, 2011, for U.S. Appl. No. 11/672,020, filed Feb. 6, 2007, 3 pages.
Restriction Requirement mailed on Oct. 30, 2008, for U.S. Appl. No. 11/215,660, filed Aug. 29, 2005, 7 pages.
Restriction Requirement mailed on Jun. 25, 2010, for U.S. Appl. No. 11/751,605, filed May 21, 2007, 9 pages.
Restriction Requirement mailed on Jul. 13, 2010, for U.S. Appl. No. 11/834,540, filed Aug. 6, 2007, 8 pages.
Restriction Requirement mailed on Aug. 10, 2010, for U.S. Appl. No. 11/626,189, filed Jan. 23, 2007, 5 pages.
Restriction Requirement mailed on Sep. 21, 2010, for U.S. Appl. No. 11/828,835, filed Jul. 26, 2007, 6 pages.
Restriction Requirement mailed on Dec. 10, 2010, for U.S. Appl. No. 11/736,438, filed Apr. 17, 2007, 16 pages.
Restriction Requirement mailed on Mar. 11, 2011, for U.S. Appl. No. 12/101,050, filed Apr. 10, 2008, 6 pages.
Restriction Requirement mailed on Jun. 6, 2011, for U.S. Appl. No. 11/751,596, filed May 21, 2007, 6 pages.
Restriction Requirement mailed on Sep. 29, 2011, for U.S. Appl. No. 11/672,020, filed Feb. 6, 2007, 6 pages.
Restriction Requirement mailed on Nov. 28, 2011, for U.S. Appl. No. 12/251,383, filed Oct. 14, 2008, 6 pages.
Substitute Preliminary Amendment filed Mar. 8, 2010, for U.S. Appl. No. 11/672,020, filed Feb. 6, 2007, 2 pages.
Written Opinion of the International Searching Authority mailed on May 18, 2006, for PCT Patent Application No. PCT/US2005/045499, filed on Dec. 8, 2005, 9 pages.
Written Opinion of the International Searching Authority mailed on May 19, 2006, for PCT Patent Application No. PCT/US2005/044624, filed on Dec. 8, 2005, 8 pages.
Written Opinion of the International Searching Authority mailed on Jun. 20, 2007, for PCT Patent Application No. PCT/US2006/047748, filed on Dec. 13, 2006, 7 pages.
Written Opinion of the International Searching Authority mailed on Sep. 28, 2007, for PCT Patent Application No. PCT/US2007/002096 filed on Jan. 23, 2007, 8 pages.
Written Opinion of the International Searching Authority mailed on Oct. 25, 2007, for PCT Patent Application No. PCT/US2007/003322, filed on Feb. 6, 2007, 9 pages.
Written Opinion of the International Searching Authority mailed on Oct. 26, 2007, for PCT Patent Application No. PCT/US2007/003631, filed on Feb. 9, 2007, 7 pages.
Written Opinion of the International Searching Authority mailed on Dec. 11, 2007, for PCT Patent Application No. PCT/US2007/012358, filed on May 21, 2007, 6 pages.
Written Opinion of the International Searching Authority mailed on Jan. 28, 2008, for PCT Patent Application No. PCT/US2007/012189, filed on May 21, 2007, 7 pages.
Written Opinion of the International Searching Authority mailed on Oct. 23, 2008, for PCT Patent Application No. PCT/US2008/069435, filed on Jul. 8, 2008, 6 pages.
Written Opinion of the International Searching Authority mailed on Feb. 25, 2009, for PCT Patent Application No. PCT/US2008/071390, filed on Jul. 28, 2008, 7 pages.

(56) References Cited

OTHER PUBLICATIONS

Written Opinion of the International Searching Authority mailed on Mar. 13, 2009, for PCT Patent Application No. PCT/US2008/083034, filed on Nov. 10, 2008, 4 pages.
Written Opinion of International Searching Authority mailed on Mar. 13, 2009, for PCT Patent Application No. PCT/US2008/079891, filed on Nov. 10, 2008, 5 pages.
Written Opinion of International Searching Authority mailed on Apr. 6, 2009, for PCT Patent Application No. PCT/US2008/079878, filed on Oct. 14, 2008, 13 pages.
Amendment in Response to Non-Final Office Action filed on Mar. 5, 2014, for U.S. Appl. No. 13/454,974, filed Apr. 24, 2012, 11 pages.
Amendment in Response to Final Office Action filed on Sep. 4, 2014, for U.S. Appl. No. 13/454,974, filed Apr. 24, 2012, 15 pages.
Amendment in Response to Non-Final Office Action mailed on Dec. 10, 2014, for U.S. Appl. No. 13/463,690, filed May 3, 2012, 12 pages.
European Office Action mailed on May 21, 2012, for European Patent Application No. 06845440.4, filed on Jul. 10, 2008, 6 pages.
European Office Action mailed on May 21, 2012, for European Patent Application No. 07717024.9, filed on Aug. 21, 2008, 5 pages.
European Office Action mailed on May 21, 2012, for European Patent Application No. 07717235.1, filed on Sep. 5, 2008, 5 pages.
European Office Action mailed on Sep. 3, 2013, for European Patent Application No. 05854262.2, filed on Dec. 8, 2005, 6 pages.
Extended European Search Report mailed Apr. 26, 2012, for European Patent Application No. 12153946.4, filed Feb. 3, 2012, 6 pages.
Extended European Search Report mailed Oct. 5, 2012, for European Patent Application No. 12162806.9, filed Apr. 2, 2012, 5 pages.
Final Office Action mailed on Apr. 23, 2012, for U.S. Appl. No. 11/938,256, filed Nov. 10, 2007, 13 pages.
Final Office Action mailed on Aug. 1, 2012, for U.S. Appl. No. 11/673,470, filed Feb. 9, 2007, 33 pages.
Final Office Action mailed on Mar. 6, 2014, for U.S. Appl. No. 11/751,605, filed May 21, 2007, 8 pages.
Final Office Action mailed on Jun. 10, 2014, for U.S. Appl. No. 11/215,660, filed Aug. 29, 2005, 14 pages.
Final Office Action mailed on Jul. 7, 2014, for U.S. Appl. No. 13/454,974, filed Apr. 24, 2012, 11 pages.
Final Office Action mailed on Dec. 24, 2014, for U.S. Appl. No. 13/463,690, filed May 3, 2012, 11 pages.
Japanese Office Action mailed Jan. 8, 2013 for Japanese Patent Application No. 2008-545817, filed on Dec. 13, 2006, with English Translation, 6 pages.
Japanese Office Action mailed on Mar. 5, 2013, for Japanese Patent Application No. 2008-553430, filed on Feb. 6, 2007, with English Translation, 4 pages.
Japanese Office Action mailed on May 13, 2014, for Japanese Patent Application No. 2013-138949, filed on Dec. 13, 2006, 6 pages.
Japanese Office Action mailed on May 27, 2014, for Japanese Patent Application No. 2013-111118, filed on Jan. 23, 2007, 13 pages.
Non-Final Office Action mailed on May 14, 2013, for U.S. Appl. No. 11/751,605, filed May 21, 2007, 11 pages.
Non-Final Office Action mailed on Jul. 19, 2013, for U.S. Appl. No. 11/938,256, filed Nov. 10, 2007, 12 pages.
Non-Final Office Action mailed on Aug. 30, 2013, for U.S. Appl. No. 11/673,470, filed Feb. 9, 2007, 37 pages.
Non-Final Office Action mailed on Sep. 5, 2013, for U.S. Appl. No. 13/454,974, filed Apr. 24, 2012, 11 pages.
Non-Final Office Action mailed on Nov. 14, 2013, for U.S. Appl. No. 11/215,660, filed Aug. 29, 2005, 10 pages.
Non-Final Office Action mailed on Jun. 11, 2014, for U.S. Appl. No. 13/463,690, filed May 3, 2012, 13 pages.
Non-Final Office Action mailed on Oct. 22, 2014, for U.S. Appl. No. 13/467,909, filed May 9, 2012, 8 pages.
Non-Final Office Action mailed on Dec. 22, 2014, for U.S. Appl. No. 14/025,539, filed Sep. 12, 2013, 12 pages.
Non-Final Office Action mailed on Jan. 26, 2015, for U.S. Appl. No. 13/454,974, filed Apr. 24, 2012, 14 pages.
Response to European Office Action filed on Feb. 20, 2014, for European Patent Application No. 05854262.2, filed on Dec. 8, 2005, 5 pages.
Response to Japanese Office Action mailed on Nov. 6, 2014, for Japanese Patent Application No. 2013-138949, filed on Dec. 13, 2006, 7 pages.
Response to Japanese Office Action mailed on Nov. 17, 2014, for Japanese Patent Application No. 2013-111118, filed on Jan. 23, 2007, 4 pages.
Response to Restriction Requirement filed on Jul. 19, 2013, for U.S. Appl. No. 13/454,974, filed Apr. 24, 2012, 7 pages.
Response to Restriction Requirement mailed on Apr. 21, 2014, for U.S. Appl. No. 13/463,690, filed May 3, 2012, 9 pages.
Response to Restriction Requirement filed on Sep. 2, 2014, for U.S. Appl. No. 13/467,909, filed May 9, 2012, 4 pages.
Restriction Requirement mailed on Jun. 21, 2013, for U.S. Appl. No. 13/454,974, filed Apr. 24, 2012, 11 pages.
Restriction Requirement mailed on Feb. 20, 2014, for U.S. Appl. No. 13/463,690, filed May 3, 2012, 6 pages.
Restriction Requirement mailed on Jul. 1, 2014, for U.S. Appl. No. 13/467,909, filed May 9, 2012, 9 pages.

\* cited by examiner

METHOD AND DEVICE FOR EXAMINING OR IMAGING AN INTERIOR SURFACE OF A CAVITY

CROSS-REFERENCE TO RELATED APPLICATIONS

This application is a continuation of U.S. patent application Ser. No. 13/275,206, filed on Oct. 17, 2011, which is a continuation of U.S. patent application Ser. No. 12/101,050, filed on Apr. 10, 2008, which claims the benefit of U.S. Provisional Patent Application No. 60/911,054, filed Apr. 10, 2007, the entire disclosures of which are incorporated herein by reference in their entirety.

TECHNICAL FIELD OF THE INVENTION

The present invention relates to a method and device for examining or imaging an interior surface of a cavity such as a colon.

BACKGROUND OF THE INVENTION

A scope is often used to view and examine the interior of a cavity. An endoscope is a medical device comprising a flexible tube, which is insertable into an internal body cavity through a body orifice to examine the body cavity and tissues for diagnosis. An endoscope may include a camera and a light source mounted on the distal end of its flexible tube to allow visualization of the internal environment of the body cavity. The tube of the endoscope has one or more longitudinal channels, through which an instrument can reach the body cavity to take samples of suspicious tissues or to perform other surgical procedures such as polypectomy.

To insert an endoscope into an internal body cavity, a physician advances the endoscope's flexible tube into the body cavity with the distal end of the flexible tube at the front. The physician may steer the flexible tube to follow the cavity's contour by controlling a bendable distal end portion of the flexible tube. After the endoscope is advanced to the end of the colon, the physician begins to retract the endoscope and visually scans the colon for abnormalities as the endoscope is retracted.

It is important for the physician to examine all areas of the colon where abnormalities may occur. Failure to do so may have grave consequences. However, it is difficult for the physician to simultaneously focus on examining the colon and keep track of the areas that have not been examined (or the areas of the colon that have been examined). Therefore, it is desirable to have a device or method that assists the physician in keeping track of the unexamined areas of the colon (or the examined areas).

Additionally, to ensure a careful examination of the colon, it is desirable to monitor the amount of time the physician spends examining an area of the colon, and to warn the physician if she spends insufficient time examining the area.

SUMMARY OF THE INVENTION

According to one embodiment of the present invention, an endoscope may be used to examine or image an interior surface of a cavity such as a colon. To examine (or image) a colon, for example, an operator such as a physician may first advance the endoscope to the end of the colon or to a point beyond an area of the colon to be examined. Then the operator may retract the endoscope and start examining the colon by viewing the partial images of the colon captured by the imaging device of the endoscope. The partial images captured by the imaging device are relayed to a video processing device that joins the partial images to generate a two dimensional image of the colon's interior surface. If the video processing device cannot generate a single complete view of the colon's interior surface (i.e. an area of the colon is missing from the single view), it emits a warning signal, which communicates to the physician that an area of the colon's interior surface has been missed. The physician can then move the imaging device to the missing area and capture one or more additional images. The video processing device can then integrate the additional images into the single image of the colon's interior surface. At the end of the procedure, the processing device has created a complete two-dimensional image of the colon's interior surface.

According to another embodiment of the invention, the video processing device can calculate the scanning speed and/of the total amount of time that the imaging device spends in a segment of the colon such as the ascending or transverse portion of the colon. This information can also be used to warn the physician of potential hasty examination. Those and other embodiments of the present invention overcome the disadvantages associated with the prior art.

The following is a more detailed description of some features of the present invention's embodiments. According to one aspect of the invention, a method for examining or imaging an interior surface of a cavity includes the steps of capturing partial images of an interior surface of a cavity; joining the captured partial images to form a complete image of said interior surface of the cavity; and providing an warning if the joined partial images does not form a complete image of said interior surface of the cavity.

In one preferred embodiment, the step of capturing partial images includes the steps of storing the captured partial images; and recording a sequence in which the partial images were captured.

In another preferred embodiment, the cavity is a tubular cavity and each partial image is a partial image of said interior surface of the tubular cavity. And the step of joining the captured partial images includes flattening the partial images of the interior surface of the tubular cavity; and joining the flattened partial images to form a complete flat image of said interior surface of the tubular cavity.

In still another preferred embodiment, the step of flattening each partial image includes outlining the lumen of the tubular cavity in said partial image by analyzing said partial image for the difference in contrast between the lumen of the tubular cavity and said interior surface of the tubular cavity; and excising the lumen from said partial image.

In yet another preferred embodiment, the step of flattening each partial image includes excising an outer edge of the tubular cavity in said partial image.

In still yet another preferred embodiment, the excised outer edge of said interior surface of the tubular cavity is larger than, but similar in shape to, the excised lumen.

In another preferred embodiment, the tubular cavity is a colon, and the excised outer edge of the interior surface of the colon is an outline of a haustral fold of the colon.

In a further preferred embodiment, the step of flattening each partial image includes flattening the excised partial image to create a rectangular image.

In a still further preferred embodiment, the step of flattening the excised partial image to create a rectangular image includes straightening each of the inner and outer edges of said interior surface of the tubular cavity into a substantially straight line.

In a yet further preferred embodiment, the step of joining the captured partial images includes identifying similar regions or corresponding key points between any two images.

In a yet still further preferred embodiment, the step of joining the captured partial images includes calculating a suitable transformation matrix which brings the any two images together such that the key points or similar regions overlap.

In another preferred embodiment, the step of joining the captured partial images includes joining the two images by meshing or overlapping the images as dictated by the transformation matrix.

In still another preferred embodiment, the method further includes capturing one or more additional partial images of a missing area in the image of the interior surface of the cavity if the joined partial images does not form a complete image of said interior surface of the cavity; joining the one or more additional partial images with the incomplete image of said interior surface of the cavity to form a complete image of said interior surface of the cavity; and providing an warning if the joined partial images still does not form a complete image of said interior surface of the cavity.

In yet another preferred embodiment, the method further includes providing direction to an operator to reach the missing area.

In yet still another preferred embodiment, the step of providing direction includes using an on-screen navigation cue to direct an operator to the missing area.

In a further preferred embodiment, the on-screen navigation cue includes an arrow and the missing area, both of which are displayed on a screen.

In a further preferred embodiment, the method further includes calculating a scanning speed.

In a still further preferred embodiment, the step of calculating the scanning speed includes identifying similar regions or corresponding key points between any two images; calculating a distance by which a key point or corresponding area has moved from the earlier one of the two images to the later of the two images; and calculating the scanning speed by dividing the distance by the time lapsed between the two images.

In a yet further preferred embodiment, the step of calculating the distance includes counting the number of image pixels by which the key point or corresponding area has moved.

In another preferred embodiment, the method further includes providing a warning if the scanning speed is greater than a given value.

In still another preferred embodiment, the method further includes calculating an amount of time spent on examining a region of said interior surface of the cavity.

In yet another preferred embodiment, the method further includes recognizing known features of said interior surface of the cavity to determine the region being examined.

In a further preferred embodiment, the method further includes providing a warning if the amount of time spent on examining the region is less than a given value.

According to another aspect of the invention, a method for examining or imaging an interior surface of a cavity includes capturing partial images of an interior surface of a cavity; joining the captured partial images to form a complete image of said interior surface of the cavity; capturing one or more additional partial images of a missing area in the image of said interior surface of the cavity if the joined partial images does not form a complete image of said interior surface of the cavity; and joining the one or more additional partial images with the incomplete image of said interior surface of the cavity to form a complete image of said interior surface of the cavity.

In a preferred embodiment, the method further includes providing direction to an operator to reach the missing area.

In another preferred embodiment, the step of providing direction includes using an on-screen navigation cue to direct an operator to the missing area.

In still another preferred embodiment, the on-screen navigation cue includes an arrow and the missing area, both of which are displayed on a screen.

According to still another aspect of the invention, a method for examining or imaging an interior surface of a colon includes capturing partial images of an interior surface of a colon; and joining the captured partial images to form a complete image of said interior surface of the colon.

In a preferred embodiment, each partial image is a partial image of said interior surface of the colon, and the step of joining the captured partial images includes flattening the partial images of the interior surface of the colon; and joining the flattened partial images to form a complete flat image of said interior surface of the colon.

In another preferred embodiment, the step of flattening each partial image includes outlining the lumen of the colon in said partial image by analyzing said partial image for the difference in contrast between the lumen of the colon and said interior surface of the colon; and excising the lumen from said partial image.

In still another preferred embodiment, the step of flattening each partial image includes excising an outer edge of the colon in said partial image.

In yet another preferred embodiment, the excised outer edge of said interior surface of the colon is larger than, but similar in shape to, the excised lumen.

In a further preferred embodiment, the excised outer edge of the interior surface of the colon is an outline of a haustral fold of the colon.

In a still further preferred embodiment, the step of flattening each partial image includes flattening the excised partial image to create a rectangular image.

In a yet further preferred embodiment, the step of flattening the excised partial image to create a rectangular image includes straightening each of the inner and outer edges of said interior surface of the colon into a substantially straight line.

In a yet still further preferred embodiment, the step of joining the captured partial images includes identifying similar regions or corresponding key points between any two images.

In another preferred embodiment, the step of joining the captured partial images includes calculating a suitable transformation matrix which brings the two images together such that the key points or similar regions overlap.

In still another preferred embodiment, wherein the step of joining the captured partial images includes joining the two images by meshing or overlapping the images as dictated by the transformation matrix.

In yet another preferred embodiment, the method further includes providing an warning if the joined partial images does not form a complete image of said interior surface of the colon.

In yet still another preferred embodiment, the method further includes capturing one or more additional partial images of a missing area in the image of the interior surface of the colon if the joined partial images does not form a complete image of said interior surface of the colon; joining the one or more additional partial images with the incomplete image of said interior surface of the colon to form a complete image of said interior surface of the colon; and providing an warning if the joined partial images still does not form a complete image of said interior surface of the colon.

In a further preferred embodiment, the method further includes providing an warning if the joined partial images does not form a complete image of said interior surface of the colon.

In another preferred embodiment, the method further includes capturing one or more additional partial images of a missing area in the image of the interior surface of the colon if the joined partial images does not form a complete image of said interior surface of the colon; joining the one or more additional partial images with the incomplete image of said interior surface of the colon to form a complete image of said interior surface of the colon; and providing an warning if the joined partial images still does not form a complete image of said interior surface of the colon.

According to yet another aspect of the invention, a method for examining or imaging an interior surface of a colon includes visually scanning an interior surface of a colon; calculating a scanning speed; and providing a warning if the scanning speed is greater than a given value.

In another preferred embodiment, the step of calculating the scanning speed includes capturing partial images of said interior surface of a colon; identifying similar regions or corresponding key points between any two images; calculating a distance by which a key point or corresponding area has moved from the earlier one of the two images to the later of the two images; and calculating the scanning speed by dividing the distance by the time lapsed between the two images.

In still another preferred embodiment, the step of calculating the distance includes counting the number of image pixels by which the key point or corresponding area has moved.

According to a further aspect of the invention, a method for examining an interior surface of a colon includes visually scanning an interior surface of a colon; and calculating an amount of time spent on examining a region of said interior surface of the colon.

In another preferred embodiment, the method further includes recognizing known features of said interior surface of the colon to determine the region being examined.

In a further preferred embodiment, the method further includes providing a warning if the amount of time spent on examining the region is less than a given value.

According to a further aspect of the invention, a device for examining or imaging an interior surface of a cavity includes an element for capturing partial images of an interior surface of a cavity; an element for joining the captured partial images to form a complete image of said interior surface of the cavity; and an element for providing an warning if the joined partial images does not form a complete image of said interior surface of the cavity.

According to a still further aspect of the invention, a device for examining or imaging an interior surface of a cavity includes an element capturing partial images of an interior surface of a cavity; an element joining the captured partial images to form a complete image of said interior surface of the cavity; an element capturing one or more additional partial images of a missing area in the image of said interior surface of the cavity if the joined partial images does not form a complete image of said interior surface of the cavity; and an element joining the one or more additional partial images with the incomplete image of said interior surface of the cavity to form a complete image of said interior surface of the cavity.

According to a yet further aspect of the invention, a device for examining or imaging an interior surface of a colon includes an element capturing partial images of an interior surface of a colon; and an element joining the captured partial images to form a complete image of said interior surface of the colon.

DETAILED DESCRIPTION OF EMBODIMENTS OF THE INVENTION

According to one embodiment of the present invention, an endoscope may be used to examine or image an interior surface of a cavity such as a colon. To examine (or image) a colon, for example, an operator such as a physician may first advance the endoscope to the end of the colon or to a point beyond an area of the colon to be examined. Then the operator may retract the endoscope and start examining the colon by viewing the partial images of the colon captured by the imaging device of the endoscope. The partial images captured by the imaging device are relayed to a video processing device that joins, either in real time or subsequent to a colon examination, the partial images to generate a complete two-dimensional image of the colon's interior surface. If the video processing device cannot generate a complete view of the colon's interior surface, it emits a warning signal, which communicates to the physician that an area of the colon's interior surface has been missed. The physician can then move the imaging device to the missing area and capture one or more additional images. The video processing device can then integrate the additional images into the two dimensional image of the colon's interior surface. At the end of the procedure, the processing device has created a complete two-dimensional image of the colon's interior surface.

The complete image of the colon's interior surface may be used for various purposes. For example, a series of complete images of the colon's interior surface may be obtained and stored over a period of time. A newer image may be compared an older image to determine whether there have been any new polyps or whether there has been any enlargement of a polyps. Additionally, stored images may be used to prove in a malpractice lawsuit that the physician did not miss a polyps during a colon examination.

Figure 1:
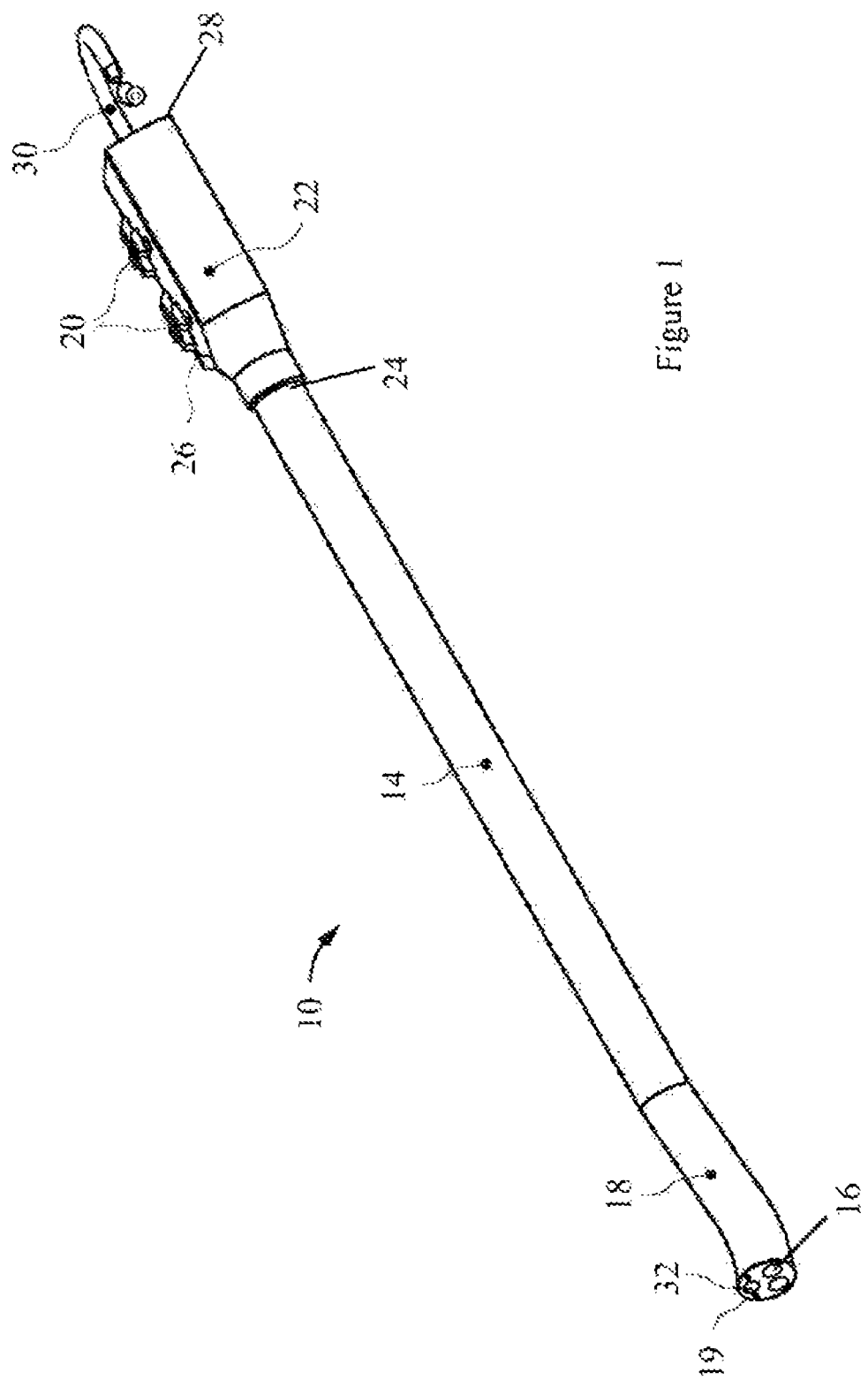
FIG. 1 shows a perspective view of an endoscope that can be used with the present invention.

FIG. 1 illustrates an exemplary endoscope 10 that can be used with one or more embodiments of the present invention. In particular, this endoscope 10 can be used in the examining or imaging of the interior surface of a cavity. For example, the endoscope 10 can be used in a variety of medical procedures in which examining or imaging of a body tissue, organ, cavity or lumen is required. The types of procedures include, for example, anoscopy, arthroscopy, bronchoscopy, colonoscopy, cystoscopy, EGD, laparoscopy, and sigmoidoscopy.

Figure 2:
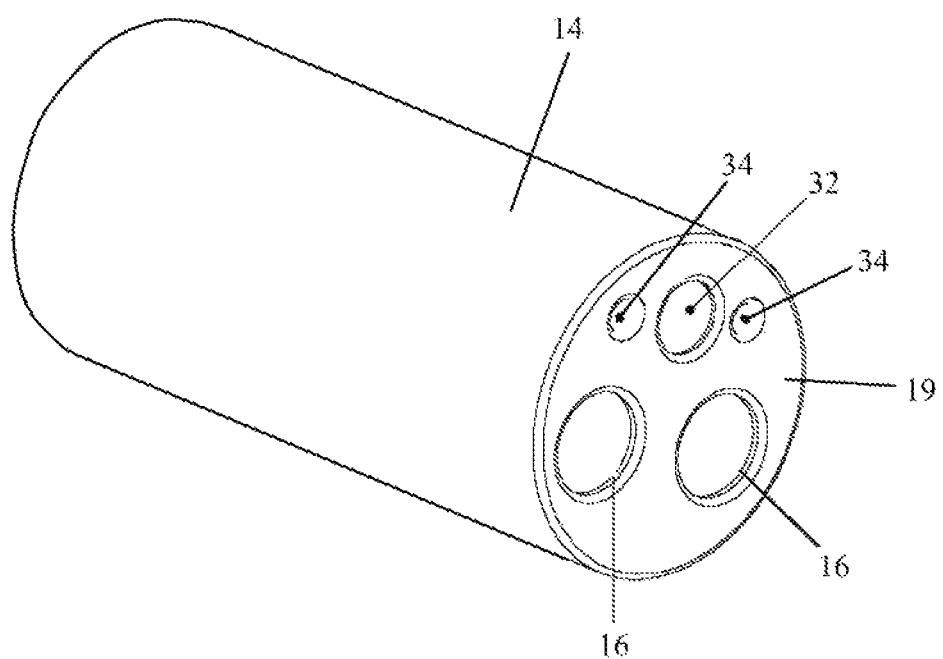
FIG. 2 shows a perspective view of the distal end of an insertion tube of the endoscope of FIG. 1.

The endoscope 10 includes an insertion tube 14 that, as shown in FIG. 2, has two longitudinal channels 16. In general, however, the insertion tube 14 may have any number of longitudinal channels. Each longitudinal channel 16 allows an instrument to reach the body cavity to perform any desired procedures such as to take samples of suspicious tissues or to perform other surgical procedures such as polypectomy. The instruments may be, for example, a retractable needle for drug injection, hydraulically actuated scissors, clamps, grasping tools, electrocoagulation systems, ultrasound transducers, electrical sensors, heating elements, laser mechanisms and other ablation means. In some embodiments, one of the channels can be used to supply a washing liquid such as water for washing. Another or the same channel may be used to supply a gas, such as $CO_2$ or air into the organ. The channels 16 may also be used to extract liquids or inject liquids, such as a drug in a liquid carrier, into the body.

The insertion tube 14 preferably is steerable or has a steerable distal end region 18 as shown in FIG. 1. The length of the distal end region 18 may be any suitable fraction of the length of the insertion tube 14, such as one half, one third, one fourth, one sixth, one tenth, or one twentieth. The insertion tube 14 may have control cables (not shown) for the manipulation of the insertion tube 14. Preferably, the control cables are symmetrically positioned within the insertion tube 14 and extend along the length of the insertion tube 14. The control cables may be anchored at or near the distal end 19 of the insertion tube 14. Each of the control cables may be a Bowden cable, which includes a wire contained in a flexible overlying hollow tube. The wires of the Bowden cables are attached to controls 20 in the handle 22 (FIG. 1). Using the controls 20, the wires can be pulled to bend the distal end region 18 of the insertion tube 14 in a given direction.

As shown in FIG. 1, the endoscope 10 may also include a control handle 22 connected to the proximal end 24 of the insertion tube 14. Preferably, the control handle 22 has one or more ports and/or valves (not shown) for controlling access to the channels 16 of the insertion tube 14. The ports and/or valves can be air or water valves, suction valves, instrumentation ports, and suction/instrumentation ports. As shown in FIG. 1, the control handle 22 may additionally include buttons 26 for taking pictures with an imaging device on the insertion tube 14.

The proximal end 28 of the control handle 22 may include an accessory outlet 30 (FIG. 1) that provides fluid communication between the air, water and suction channels and the pumps and related accessories. The same outlet 30 or a different outlet can be used for electrical lines to light and imaging components at the distal end of the endoscope 10.

As shown in FIG. 2, the endoscope 10 also includes an imaging device 32 and light sources 34, both of which are disposed at the distal end 19 of the insertion tube 14. Alternatively, the imaging device 32 and light source 34 may be positioned on the cylindrical sidewall of the insertion tube 14. The imaging device 32 may include, for example, a lens, single chip sensor, multiple chip sensor or fiber optic implemented devices. The imaging device 32, in electrical communication with a processor and/or monitor, may provide still images or recorded or live video images. The light sources 34 may be light emitting diodes (LEDs) or fiber optical delivery of light from an external light source. The light sources 34 preferably are equidistant from the imaging device 32 to provide even illumination. The intensity of each light source 34 can be adjusted to achieve optimum imaging. The circuits for the imaging device 32 and light sources 34 may be incorporated into a printed circuit board (PCB).

According to one embodiment of the present invention, this endoscope 10 may be used to examine or image an interior surface of a cavity such as a colon. To examine (or image) a colon, for example, an operator such as a physician may insert the endoscope 10 into the patient's rectum and then advance it to the end of the colon or to a point beyond an area of the colon to be examined. Then the operator may retract the endoscope 10 and start examining the colon by viewing the images captured by the imaging device 32 of the endoscope 10. Alternatively, the operator may examine the colon by advancing the endoscope 10 (as opposed to retracting the endoscope 10). In general, the operator may move or position the endoscope 10 in any suitable manner during the examination of the colon.

As the colon is being examined, partial still images of the colon are captured. The still images may be captured from the video signal generated by the imaging device 32. Alternatively, a still camera may be used to capture the images. The still images may be captured either automatically or manually. To manually capture the partial still images, the operator may decide when a still image is captured by pressing a button. Manual operation has the advantage that an image is captured only when the view is sufficient clear and when there is no fluid or excrement in the view that prevents an unobstructed view of the colon's interior surface. If there is fluid or secretion in the view, the operator may wash the colon or extract the fluid or secretion from the colon before an image is captured. The images captured by the imaging device 32 are then relayed to a processing device, which stores the images in memory. Preferably the order in which the images are captured is also stored.

Given the image capture rate of a typical imaging device, it may be unnecessary to store and use every image in order to obtain the complete two-dimensional image of the colon's interior surface. Accordingly, an image that is blurry or difficult to join may be discarded and the next image may be stored and used. A blurry image may be caused by fluid or excrement in the colon. In addition, when the imaging device 32 is paused at a location, duplicate or similar images can be discarded such that unnecessary images are not stored and used to form the final joined image. For example, if a procedure such as a biopsy or polypectomy needs to be performed using the endoscope, the physician can pause the image capture such that the final joined image is not adversely affected. Furthermore, the operator can decide whether images are being collected merely for display, for creating the final joined image, or both.

If the imaging device 32 is disposed at the distal end 19 of the insertion tube 14, the imaging device 32 faces the longitudinal direction of the colon, and the image of the colon captured by the imaging device 32 will likely show a view of the colon's interior surface along the longitudinal direction. In other words, as shown in FIG. 3a, the captured view of the colon 40 will likely show the colon's lumen 42 surrounded by the colon's interior surface 44, with the colon's interior surface 44 farther away from the imaging device 32 being at the center of the image 40 and surrounding the colon's lumen 42 and with the colon's interior surface 44 closer to the imaging device 32 being at the outer edge of the image 40.

In some embodiments of the present invention, after an image of the colon has been captured and relayed to the video processing device, the video processing device manipulates and scales the image from showing a longitudinal view of the colon's interior surface to showing a "flattened" rectangular view of the colon's interior surface. This procedure, illustrated in FIGS. 3a to 3g, may be carried out by excising the image so that it shows only the interior surface of a given length of the colon. FIG. 3a illustrates an image 40 captured by the imaging device 32 and relayed to the video processing device. As a first step, as shown in FIG. 3b, the processing device outlines the lumen 42 by analyzing the image 40 for the difference in contrast between the colon's lumen 42 and its interior surface 44. After it has outlined the lumen 42, the processing device excises the lumen 42 from the image 40, as shown in FIG. 3c. In some embodiments, both the lumen 42 and the area surrounding the lumen 42 may be excised from the image 40. Then, the outer edge 46 of the image 40 may be excised to produce a ring-shaped image of the colon, as shown in FIGS. 3d and 3e. Preferably, the outer edge of the excised image is similar in shape to its inner edge of the excised image. In other words, the outer edge of the excised image can be equally spaced from the inner edge in the radial direction. This allows the flattened image to have a substantially rectangular configuration. Alternatively, the outer edge of the image can follow the outline of a haustral fold of the colon as shown in FIG. 3d. A haustral fold can be identified by the unique pattern of shading and contrast exhibited in the image.

Figure 3:
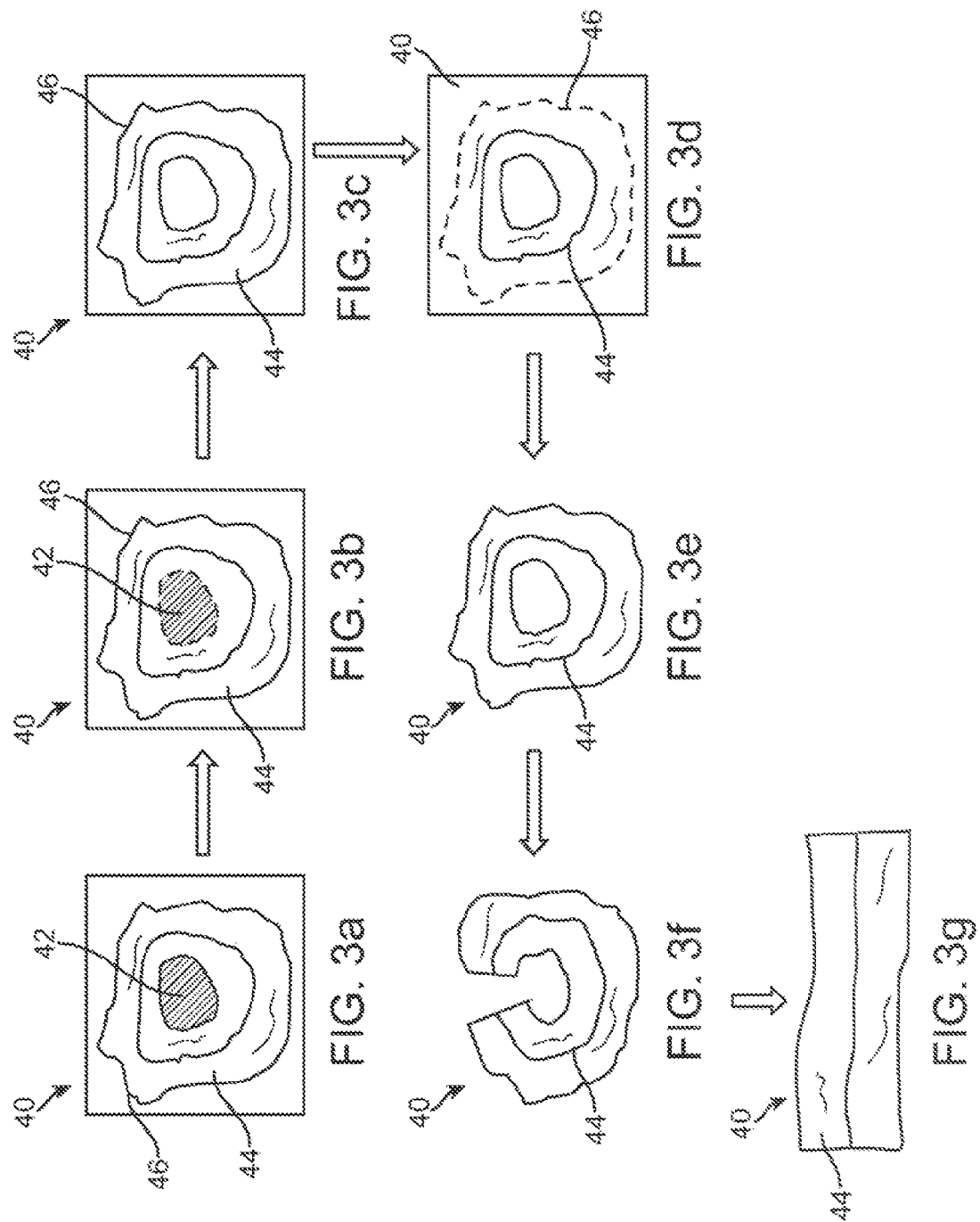
FIGS. 3a to 3g show an example of image transformation.

This excised image is then "cut" radially and longitudinally along a side of the image (FIG. 3f), and it is manipulated and flattened to show a rectangular view of the colon's interior surface (FIG. 3g). The excised image may be "cut" with or without overlap. When "cut" with overlap, the two "cut" edges of the image may overlap, and a region of the image may be on both sides of the "cut." To carry out this procedure, the processing device may convert the inner and outer edges of the image into substantially straight lines such that the ring-shaped view is converted into a rectangular view as shown in FIGS. 3f to 3g. This conversion causes certain areas of the image to undergo compression and others expansion.

Figure 4:
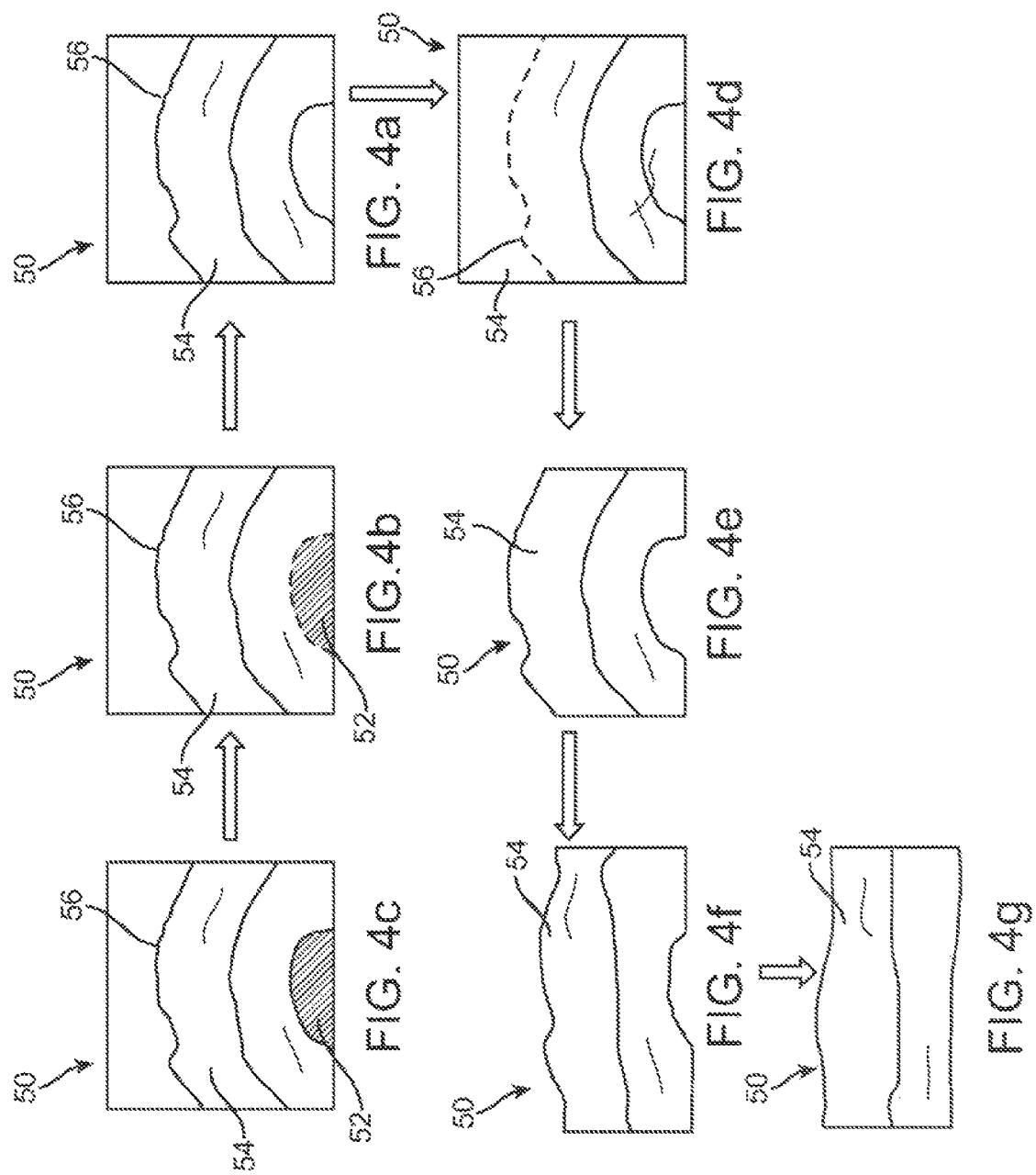
FIGS. 4a to 4g show another example of image transformation.

The previous discussion presupposes that the image of the colon shows a longitudinal view of the colon. In other words, the endoscope 10 lies parallel with the longitudinal axis of the colon, and the imaging device 32 of the endoscope 10 is disposed at the distal end 19 of the endoscope 10 and faces the longitudinal direction of the colon. In a situation where the imaging device 32 is angled away from the longitudinal axis of the colon, the image 50 may not show the entire lumen 52, and the image may need to be reconstructed in a slightly different manner (FIGS. 4a to 4g). As seen in FIG. 4a, the lumen 52 or part of the lumen 52 is identified by the difference in contrast. Once the lumen 52 has been identified, it is excised from the image 50 as shown in FIG. 4c, and a corresponding arc is also excised from the outer edge of the image 50 as shown in FIG. 4d. The image 50 is then converted to a substantially rectangle view as shown in FIGS. 4f and 4g.

In a situation where the image does not show the colon's lumen, the processing device may locate the image spatially based on the positions of the previous images, such as the positions of the preceding images. For example, if the imaging device 32 faces a direction that is perpendicular to the longitudinal direction of the colon, the processing device can locate the image based on the positions of the previous images that overlap with this particular image. Images captured from this viewpoint may not need to be converted because of their substantially rectangular and flat shape.

Once an image has been converted into a flat view, the image is analyzed in conjunction with other images, such as the preceding images, to find similar regions and define corresponding key points. This can be accomplished by any one of the various methods known in the field of imaging technology. One such method is an algorithm known as SIFT (Scale Invariant Feature Transform), which is invariant to image scaling, rotations, and partially invariant to changes in illumination and 3D camera viewpoint. Interest points, which are invariant to scale and rotation, are identified in each image by constructing a multi-scale pyramid of Difference of Gaussian (DoG) images. Key points are identified by localizing maxima or minima in the Gaussian pyramid across levels. Next, each interest point is oriented by computing a gradient orientation histogram. A set of orientation histograms in a neighborhood such as 4×4 pixel neighborhood may be used to create the key point descriptor. Finally, the feature descriptors are normalized in order to account for differences in illumination. Once feature points and descriptors are identified in each image, corresponding key points are identified. And, after similar regions or corresponding key points are identified between images, a suitable transformation matrix, which brings the images together such that key points or similar regions overlap, is calculated. An index or number may be used to measure the degree of similarity between two regions of two images. If this index or number is above a given value the two regions of the two images are considered to be overlapping.

Figure 5:
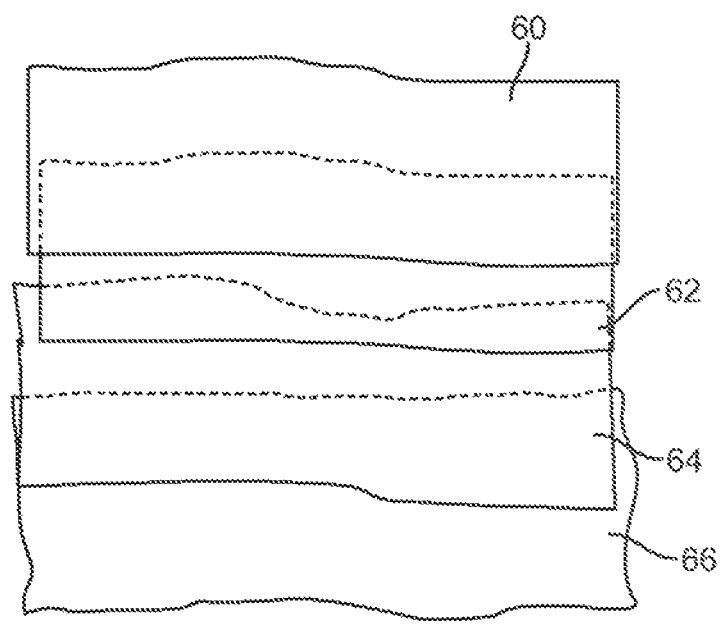
FIG. 5 shows a diagram illustrating the joining of images.

In the final step, two images are joined together by meshing or overlapping the images as dictated by the transformation matrix. Every image thereafter may be then joined to the preceding series of joined images. It is hoped that, by the end of the procedure, a single image that includes a 2-D view of the interior surface of the colon results as shown in FIG. 5, which shows that four partially overlapping images 60, 62, 64, 66 are joined to form a single image.

In another preferred embodiment, to verify that the single joined image of the interior surface of the colon is complete, the processing device checks to ensure that no areas are missing as it continuously joins images together. When an area is missing, the processing device sends a signal, such as an audio and/or visual signal, that alerts the physician to the missed area. The physician can then return to the missing area and capture one or more additional images. In addition, in the event that an image is fuzzy or otherwise unsuitable for the construction of the single joined image, the processing device also alerts the physician so that one or more additional images may be acquired to take the place of the unsuitable image.

A missing area in the joined image can be detected in various manners. For example, there is likely a missing area if an excised inner or outer edge of a partial image is not joined to another partial image or if a region bordering on an excised inner or outer edge of a partial image does not have a corresponding region in another partial image and therefore cannot be joined to another partial image. This, however, does not always apply to the cut edge of a partial image (FIG. 3f), which is made so that the partial image can be flattened (FIGS. 3a-3g). This may also not apply to the first and last images because these two images each have an edge not joined to another image. Another way to detect a missing area is to see whether the cut edges of each partial image can be rejoined after the partial images have been joined to form a single image. If the cut edges of each partial image cannot be rejoined, the single image will likely have a missing area.

Figure 6:
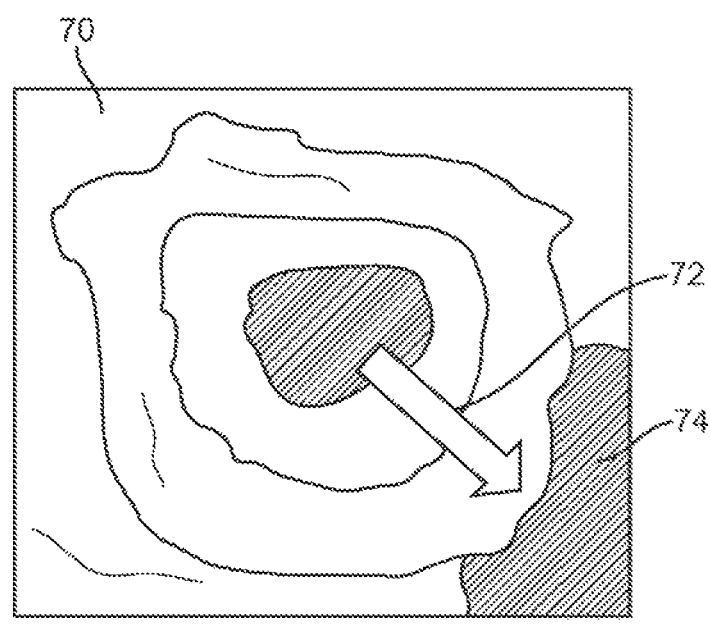
FIG. 6 shows an on-screen cue for directing an operator to a missing area of a joined image.

In another preferred embodiment, when there is a missing area in the single joined image or an unsuitable image, the processing device uses an on-screen navigation cue to direct the operator to the location of the missing area or unsuitable image. As shown in FIG. 6, the on-screen navigation cue may include an arrow 72 on the screen 70 indicating the desired direction of movement for the imaging device 32. Additionally or alternatively, the on-screen navigation cue may include a highlighted area 74 on the screen 70 representing the location of the missing area or unsuitable image. The processing device may implement this feature by comparing the images joined previously with the current image being captured by the imaging device 32. By comparing corresponding key points between these images, the processing device can direct the operator to move the imaging device 32 to the desired location.

In a further preferred embodiment, the processing device can calculate the scanning speed and/of the total amount of time that the imaging device spends in a segment of the colon such as the ascending or transverse portion of the colon. To calculate the scanning speed, the processing device may rely on an algorithm that determines tracking time or speed in a manner similar to an optical computer mouse. The processing device can perform the same or similar steps of analyzing captured images. Before joining the images, the processing device analyzes the distance by which key points or corresponding areas have moved from one image to a subsequent image. The processing device can calculate the scanning speed by dividing the distance traveled by the time lapsed between the two images. The distance by which a given point or feature travels can be denoted by the number of image pixels. Each pixel can then be standardized to a measurement of actual distance such that the calculation can be performed.

The distance traveled can also be calculated by measuring the size change of a geometric feature from one image to another image. For example, if the geometric feature appears larger in an earlier image and smaller in a later image, it can be concluded that the imaging device is moving away from the geometric feature. The distance traveled by the imaging device can be calculated from the change in size.

To calculate the total amount of time spent in a segment of the colon, the processing device needs to recognize when the imaging device is in the segment of the colon. In one preferred embodiment, the processing device recognizes a segment of the colon by its distinctive features, which can be, for example, the various flexures (e.g., splenic, hepatic, etc). Preferably, the processing device recognizes a feature by comparing the captured image of the feature with a stored standard or typical image of the feature. For example, as the endoscope is withdrawn from the end of the colon, the hepatic flexure is expected first, and images are filtered for properties that would suggest an image of the hepatic flexure. The location of areas of shading/contrast and the location of the lumen in the image would suggest to the processing device that the image is of a flexure. The processing device can alert the operator about whether she is scanning the colon too fast and provide data on how much time was spent in each segment of the colon.

Another feature that can be used to recognize the segment of the colon is the geometric shape of the colon. For example, the lumen of the transverse colon has a particularly triangular shape. An image of the colon's geometric shape can be compared with a database of images the colon's geometric shape to determine which segment of the colon the imaging device is in.

In an alternate embodiment of the invention, the endoscope may have a sensor or transducer for communicating the position (such as the location and/or orientation) of the imaging device to the processing device. Examples of such a positioning sensor include magnetic positioning sensors such as the Aurora System manufactured by NDI International of Waterloo, Canada, RF positioning sensors, or optical positioning sensors. The processing device can integrate the positional information of the imaging device with the image capturing and joining algorithm to better determine how to join the images. Joining of the images can be improved based on the imaging device's position, or based on information about the particular geometry of the colon the imaging device is in.

While particular embodiments of the present invention have been shown and described, it will be obvious to those skilled in the art that changes and modifications can be made without departing from this invention in its broader aspects. For instance, the above embodiments involve the examination of a colon. In general, however, a method or device of the present invention can be used to examine any cavity, such as any body cavity. Therefore, the appended claims are to encompass within their scope all such changes and modifications as fall within the true spirit and scope of this invention.

The invention claimed is:

1. An accessory device for a colonoscope, the device comprising:
   an imaging device configured to capture images of an interior surface of a colon, wherein the imaging device is configured to be positioned on a sidewall of a colonoscope;
   a positioning sensor for detecting positional information of the imaging device within the colon; and
   a processing device in communication with the imaging device and positioning sensor, wherein the processing device is programmed to join the images using the positional information, and wherein the processing device is further programmed to calculate an amount of time spent by the imaging device in an identified colon segment.

2. The device of claim 1, wherein the processing device comprises a memory capable of storing images and positional information.

3. The device of claim 2, wherein the memory is capable of storing the order in which images are captured.

4. The device of claim 1, wherein the positioning sensor is further configured to detect orientational information of the imaging device within the colon.

5. The device of claim 4, wherein the processing device is further programmed to join the images using the orientational information.

6. The device of claim 1, wherein the processing device is programmed to generate a complete image of the interior surface of the colon segment using the joined images.

7. The device of claim 6, wherein the processing device is programmed to detect and provide a warning if the joined images do not form a complete image of the interior surface of the colon segment.

8. The device of claim 1, wherein the positioning sensor comprises a magnetic positioning sensor.

9. The device of claim 1, wherein the positioning sensor comprises a RF positioning sensor.

10. The device of claim 1, wherein the positioning sensor comprises an optical positioning sensor.

11. The device of claim 2, wherein the processing device is further programmed to compare a newly captured image of the interior surface of the colon with the joined images.

12. The device of claim 2, wherein the processing device is further programmed to compare a newly captured image with an old image retrieved from the memory to identify changes in the interior surface of the colon.

13. The device of claim 2, wherein the processing device is further programmed to provide image and positional information to an operator so that the operator can return to a previously imaged location during a procedure.

14. The device of claim 1, wherein the processing device is programmed to recognize distinctive features of the colon segment.

15. A method of using an accessory device for a colonoscope, the method comprising:
   capturing images of an interior surface of a colon using imaging device of an accessory device for a colonoscope, wherein the imaging device is positioned on a sidewall of the colonoscope and wherein the accessory device further comprises a positioning sensor for detecting positional information of the imaging device within the colon, and a processing device in communication with the imaging device and the positioning sensor; and joining the captured images using the processing device, wherein the processing device is programmed to join the captured images using the positional information, and wherein the processing device is further programmed to calculate an amount of time spent by the imaging device in an identified colon segment.

16. The method of claim 15, wherein the processing device comprises a memory capable of storing images, positional information, and the order in which the images are captured.

17. The method of claim 15, further comprising clearing fluids from the colon prior to capturing images.

18. The method of claim 15, further comprising generating a complete image of the interior surface of the colon segment using the joined images.

19. The method of claim 18, further comprising detecting if the joined images do not form a complete image of the interior surface of the colon segment and generating a warning.

20. The method of claim 15, wherein the positioning sensor is configured to detect orientational information of the imaging device within the colon.

\* \* \* \* \*